(12) United States Patent
Kim et al.

(10) Patent No.: US 6,190,907 B1
(45) Date of Patent: Feb. 20, 2001

(54) RETROVIRAL VECTORS FOR GENE THERAPY

(75) Inventors: Sun-Young Kim; Seon-Hee Kim, both of Seoul (KR); Paul D. Robbins, Mt. Zebanon, PA (US)

(73) Assignee: Viromedica Pacific Limited, Seoul (KR)

( * ) Notice: Under 35 U.S.C. 154(b), the term of this patent shall be extended for 0 days.

(21) Appl. No.: 09/077,205

(22) PCT Filed: Sep. 22, 1997

(86) PCT No.: PCT/KR97/00180

§ 371 Date: May 20, 1998

§ 102(e) Date: May 20, 1998

(87) PCT Pub. No.: WO98/12338

PCT Pub. Date: Mar. 26, 1998

(30) Foreign Application Priority Data

Sep. 21, 1996 (KR) .................................................. 96-41438

(51) Int. Cl.[7] .................................................. C12N 15/63
(52) U.S. Cl. ............................................................. 435/320.1
(58) Field of Search ........................... 435/320.1; 514/44; 536/23.1; 424/93.6

(56) References Cited

U.S. PATENT DOCUMENTS 5,693,508 * 12/1997 Chang .................................. 435/69.1
5,891,680 * 4/1999 Lieschke et al. ................. 435/69.52

FOREIGN PATENT DOCUMENTS

WO 92/07943   5/1992  (WO) .
94/03622 *    2/1994  (WO) .
WO94/03622 *  2/1994  (WO) .
WO 94/03622   2/1994  (WO) .
WO 95/30763   11/1995 (WO) .
WO 95/34669   12/1995 (WO) .

OTHER PUBLICATIONS

Zitvogel et al. Human Gene Therapy. vol. 5: pp. 1493–1506, Dec. 1994.*
Tahara et al. The Journal of Immunology. pp. 6466–6474, 1995.*
Mann et al. Cell. vol. 33: pp. 153–159, May 1983.*
Schinnick et al. Nature, vol. 293: pp. 543–548, Oct. 1981.*
Seon Hee Kim et al., "Construction of Retroviral Vectors with Improved Safety, Gene Expression, and Versatility", *Journal of Virology*, 72(2):994–1004(1998).
A. Dusty Miller et al., "Improved Retroviral Vectorsfor Gene Transferand Expression", *Bio Techniques*, 7(9):980–990(1989).

* cited by examiner

*Primary Examiner*—Remy Yucel
(74) *Attorney, Agent, or Firm*—Darby & Darby

(57) ABSTRACT

The present invention provides novel, improved retroviral vectors which can be used for gene therapy, more specifically, retroviral vectors which are not only safer, more versatile, and more convenient than any other existing vectors, but they also drive high levels of gene expression and high viral titer. In retroviral vectors of the present invention, gag and env coding sequences are deleted, and all or part of U3 can be readily substituted with heterologous, non-retroviral promoter elements. Furthermore, at least one internal ribosome entry site is employed to express more than one genes, and multicloning sites are placed in an insertion site for cloning of a heterologous promoter or a foreign gene.

10 Claims, 34 Drawing Sheets

| | | | |
|---|---|---|---|
| SRE | CCATATATGG | (hatched circle) | ACTAACGGGACTTTCCAA<br>NF-kB |
| 21 | GCCAGGCGGGCCATTTACCGT<br>SP1 | 16 | CTTGGCAGTACATCAA |
| 19 | CCCCGTGACGCAAATGGG<br>ATF | (hatched box) | TAGTCA<br>AP1 |

MFG-mGM/CSF

SCP1-mGM/CSF

MFG-WIN

KCP3-WNIN

KCP3-WXIN

RETROVIRAL VECTORS FOR GENE THERAPY

BACKGROUND OF THE INVENTION

1. Field of the Invention

The present invention relates to novel, improved retroviral vectors which can be used for gene therapy, more specifically, to retroviral vectors which are not only safer, more versatile, and more convenient than any other existing vectors, but they also drive high levels of gene expression and high viral titer.

2. Description of the Prior Art

Murine leukemia virus(MLV)-based retroviral vectors which are the most widely used gene delivery vehicles in gene therapy clinical trials, have been employed in almost 70% of approved protocols(see: Ali, M. et al., Gene Ther., 1:367–384, 1994; Marshall, E., Science, 269:1050–1055, 1995).

However, despite their frequent use for gene transfer, many of the biochemical and genetic properties of MLV such as cis and trans factors important for gene expression, viral assembly and packing, have not been completely understood. Moreover, there are many problems with the retroviral vectors currently in clinical use such as MFG(see: Bowtell, D. et al., J. Virol., 62:2464–2473, 1988; Ohashi, T. S. et al., Proc. Natl. Acad. Sci., USA, 89:11332–11336, 1992; Jaffe, E. M., Cancer Res., 53:2221–2226, 1993; Bender, M. A. et al., J. Virol., 61:1639–1646, 1987), and LN-based vectors (see: Boggs, S. S. et al., Gene Ther., 2:632–638,1995; Armentano, D. et al., J. Virol., 61:1647–1650, 1987; Adam M. A., and A. D. Miller, J. Virol., 62:3802–3806, 19B8; Osborne, W. R. A., and A. D. Miller, Proc. Natl. Acad. Sci., USA, 85:6851–6855, 1988; Miller, A. D., and Roseman, Biotechniques, 7:980–990, 1989; Palmer, T. D. et al., Blood, 73:438–445, 1989).

First, all retroviral vectors contain sequences which are also present in the packaging lines. Accordingly, recombination between the packaging genome and the vector results in the generation of replication-competent retrovirus(RCR).

Secondly, most retroviral vectors use either long terminal repeat(LTR) sequences from MLV or related LTR sequences such as myeloid proliferation stimulating virus(MPSV), murine sarcoma virus(MSV) or an heterologous internal promoter. Although the LTR works efficiently in certain cell types, its activity can be down-regulated and its presence can affect expression from internal promoters(see: Bowtell, D. D. L. et al., J. Virol., 62:2464–2473, 1988; Emerman, M. and H. M. Temin, Cell, 39:449–467, 1984).

Thirdly, the viral titers achieved with the vectors in current packaging lines, although they are improved ones, are still not sufficiently high enough for many therapeutic applications.

Fourthly, MLV-based vectors packaged in murine packaging lines, are susceptible to complement-mediated inactivation in vivo, which, in turn, limits their utility for in vivo applications(see: Takeuchi, Y. et al., J. Virol., 68:8001–8007, 1994; Cosset F. L. et al., J. Virol., 69:7430–7436, 1995).

Fifthly, it is difficult to produce a virus at a reasonable titer for targeting a specific cell type or tissue by direct, in vivo delivery(see: Kasahara, N. et al., Science, 266:1373–1376, 1994; Kabat D., Science, 269:417, 1995).

Finally, MLV-based vectors, when packaged in murine packaging lines, cannot deliver a gene of interest to non-dividing cells.

Under the circumstances, WO 92/07943 discloses a retroviral vector MFG including an insertion site for genes of interest which are capable of expressing high levels of the protein derived from the genes of interest in a wide variety of transfected cell types, and those lacking a selective marker, thus rendering them suitable for human gene therapy in the treatment of a variety of disease states without the co-expresssing of a selective marker.

In this connection, the present inventors compared the levels of gene expression from several types of retroviral vectors currently used in clinical trials for gene therapy(see: Byun, J. et al., Gene Ther., 3:780–788, 1996). As a result, it has been suggested that the MFG retroviral vector is superior in conferring gene expression after transduction of a variety of target cells, whose results are consistent with the previous reports in the art(see: Ohashi, T. S. et al., Proc. Natl. Acad. Sci., USA, 89:11332–11336, 1992; Riviere I. et al., Proc. Natl. Acad. Sci., USA, 92:6733–6737, 1995; Krall, W. J. et al., Gene Therapy, 3:37–48, 1996).

However, it has been found that the MFG retroviral vector has many features that should be modified in terms of gene expression, viral titers and safety as follows:

First, MFG contains significantly long coding sequences for gag and env used as a template for homologous recombination, which increase the possibility of the generation of replication-competent retrovirus (RCR).

Secondly, MFG-mediated gene expression is driven by the MLV LTR which is a medium-strength constitutive promoter. However, for many therapeutic applications, it would be necessary to regulate gene expression, not only in terms of levels but also timing of expression, in a sophisticated manner. Accordingly, if heterologous promoter elements are inserted to U3 or U3 is replaced with other full-size promoters, the retroviral vector can be applied in a wide variety of gene therapy. In this connection, the enhancer region of MLV U3 is replaced with heterologous enhancers and U3 is substituted with U3 from similar retroviruses such as MPSV and Friend MLV, nevertheless, it is not clear whether U3 can be replaced with a completely different sequence.

Thirdly, the original version of MFG is designed for expression of a single gene, though the expression of more than two or three genes is desirable for many therapeutic applications.

Finally, NcoI which coincides with the ATG codon of the env gene should be the expression site in MFG to obtain high levels of gene expression, which, in turn, restricts the broader use of MFG retroviral vector.

Naturally, in order for retroviral vectors including MFG to be clinically viable forms of gene delivery, some or all of the current limitations have to be addressed. Accordingly, there are strong reasons for exploring novel and improved retroviral vectors which are capable of expressing controlled levels of proteins derived from the genes of interest in a wide range of transfected cells.

SUMMARY OF THE INVENTION

In accordance with the present invention, the inventors discovered that several retroviral vectors in which gag and env sequences unnecessary for packaging are deleted, all or part of U3 sequence inessential for retroviral functions is replaced with heterologous promoter elements, at least one internal ribosome entry site is employed to express more than one genes, and multicloning sites are placed in an insertion site for cloning of a heterologous promoter or a foreign gene, can drive high levels of gene expression and high viral titer.

A primary object of the invention is, therefore, to provide novel, improved retroviral vectors for gene therapy, in terms of safety, versatility and convenience, which can drive high levels of gene expression and high viral titer.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Figure 1:
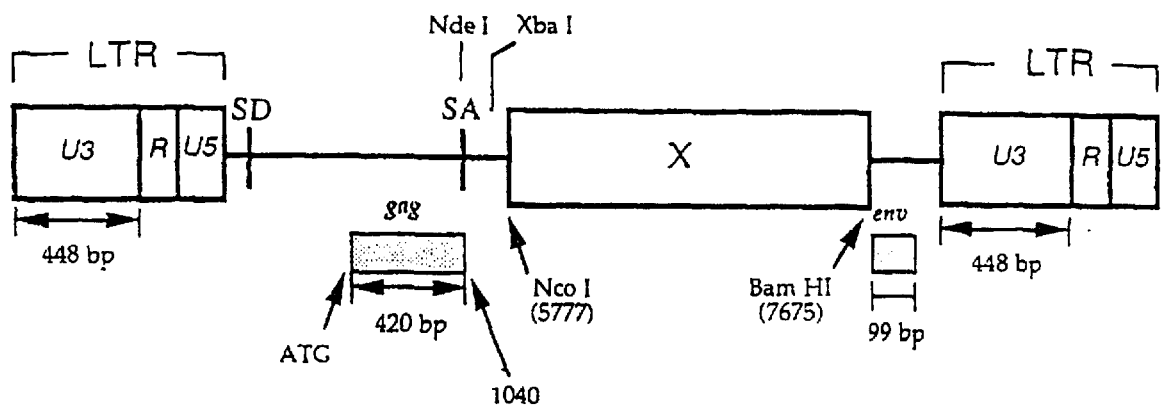
FIG. 1 is a schematic representation of a retroviral vector MFG.

The present inventors have constructed several novel and improved retroviral vectors that can be used for gene therapy, by employing a MLV-based retroviral vector, preferably a retroviral vector MFG(ATCC 68754), as a starting vector for systematic deletion analysis and modification. The retroviral vectors of the present invention accommodate the following features:

1. They contain the minimum length of retroviral sequences in which gag and env coding sequences which do not significantly affect viral functions such as packaging or gene expression are deleted. In particular, since gag coding sequence and its immediate upstream region are included in all currently available retroviral vector, and a retroviral vector like MFG contains a significantly long env coding sequence, deletions of gag and env sequences decrease the possibility of homologous recombination between the nucleotide sequences in the vector and the packaging line and of generation of RCR.

2. All or part of U3 sequence in the 3'LTR is substituted with full-size heterologous promoters or their fragments with any deleterious effects, therefore making it possible to control gene expression in a precise manner.
3. They contain restriction sites at the truncated U3 of the 3'LTR, so that heterologous promoter elements can be easily inserted thereto. This way, retroviral vectors can be readily converted for different purposes, for example, by altering levels and regulatory modes of gene expression.
4. They contain one or two IRESs so that two or three genes can be expressed in one vector as a multicistronic message.
5. They contain multicloning sites at the expression site, which eases the convenient insertion of foreign genes.

The present retroviral vectors having the aforementioned characteristics cover retroviral vectors which are capable of delivering a gene of interest to a target cell when packaging functions of Gag, Pol and Env are provided, and are free of gag coding sequence. The retroviral vectors are based on MLV in which nucleotide sequence of #523 to #1040 including entire gag coding sequence is deleted.

From the retroviral vectors, entire env coding sequence, and retroviral nuclotide sequence between termination codon of env coding sequence and polypurine tract can be further removed. In addition, in the retroviral vectors, the gene of interest is located downstream from both a splice donor site and a splice acceptor site.

The gene of interest that is incorporated in the vectors of the invention may be any gene which produces a hormone, an enzyme, a receptor or a drug(s) of interest.

The retroviral vectors of the invention are further characterized in that all or part of at least one U3 sequence of a 5'LTR and a 3'LTR derived from a retrovirus is substituted with a full-size heterologous promoter or a fragment thereof. At this time, the full-size heterologous promoter or the fragment thereof is inserted at the truncated U3 of MLV-based retroviral vector in which truncation is provided at the nucleotide sequence which is selected from the group consisting of: a nucleotide sequence between #−330 Pvu II and #−152 Xba I recognition sites on the 5'LTR, a nucleotide sequence between #−152 Xba I and #−36 Sac I recognition sites on the 5'LTR, a nucleotide sequence between #−330 Pvu II and #−36 Sac I recognition sites on the 5'LTR, a nucleotide sequence between #−419 Nhe I and #−36 Sac I recognition sites on the 5'LTR, and nucleotide sequences on the 3'LTR corresponding to said nucleotide sequences on the 5'LTR.

In describing the retroviral vector of the present invention, the numbering is carried out, based on Shinnick et al's publication(see: Shinnick et al, Nature, 293:543–548, 1981).

In the retroviral vectors of the invention, the heterologous promoter is regulated at the transcription level by the aid of a chemical or a biological molecule, where the biological molecule may be any materials of hormone, growth factor, enzyme, lymphokine or cytokine.

Moreover, the retroviral vectors may further comprise one or two internal ribosomal entry site(IRES) which are obtainable from murine encephalomyocarditis virus (EMCV) or foot and mouth disease virus(FMDV). It is preferred that each of the two IRES is obtained from different viral sources, in case of employing two IRES.

The retroviral vectors may further comprise a multicloning site at the truncated U3 of the 3'LTR, so that the full-size heterologous promoter or the fragment thereof can be easily inserted thereto, or a multicloning site downstream from the splice acceptor site or upstream from the IRES, so that a gene of interest can be easily inserted thereto.

The present invention is further illustrated in the following examples, which should not be taken to limit the scope of the invention.

Cell lines, culture media therefor and a method for the determination of transfection efficiency and viral titer which are employed in Examples below, are as follows:

CRIP(CRL 9808), NIH3T3(CRL1658) and U937 (CRL1593) were obtained from the American Type Culture Collection(ATCC) (Rockville, Md., U.S.A.), while CEM-SS(#776 or #87) was from the NIH AIDS Research and Reference Reagent Program(Rockville, Md., U.S.A.). BING is an amphotropic cell line derived from 293T cell(see: DuBridge, R. B. et al., Mol. Cell. Biol., 7:379–387, 1987) which is similar to the ecotropic BOSC 23 packaging cell line(see: Pear, W. S. et al., Proc. Natl. Acad. Sci., USA, 90:8392–8396, 1993).

NIH3T3 and CRIP were grown in Dulbecco's modified Eagle's medium(D-MEM) supplemented with 10% fetal bovine serum(FBS). CEM-SS, H9 and U937 were grown in RPMI 1640 medium supplemented with 10% FBS. Each medium used in the Examples was supplemented with 120 µg/ml penicillin G(Sigma P-3032; 1690 U/mg) and 200 µg/ml streptomycin sulfate(Sigma S-9137; 750 U/mg).

BING and CRIP were transfected by a calcium phosphate-DNA coprecipitation method as previously described in detail(see: Byun, J. et al., Gene Ther., 3:780–788, 1996; Pear, W. S. et al., Proc. Natl. Acad. Sci., USA, 90:8392–8396, 1993; Miller, A. D. and C. Buttimore., Mol. Cell. Biol., 6:2895–2902, 1986). A total of 10 µl DNA in 500 µl $CaCl_2/H_2O$ (124 mM $CaCl_2$) was mixed with 500 µl of 2×HBS(280 mM NaCl, 10 mM KCl, 1.5 mM $Na_2HPO_4.2H_2O$, 12 mM dextrose, 5 mM HEPES) with constant bubbling and within 1 to 2 minutes, this solution was added to the cells with 25 mg/ml of chloroquine. Transfection efficiency was measured in most experiments by X-gal (5-bromo-4-chloro-3-indolyl-β-γ-galactopyranoside) staining using the same culture plates or duplicate dishes, if necessary.

Supernatants from the transfected packaging cells were collected, usually 48 hrs after transfection, filtered through a 0.45 µm filter, and used for transduction of target cells. For transduction of CEM-SS, H9 and U937, $5 \times 10^6$ cells were harvested, resuspended with 5 ml viral supernatant in the presence of 8 µg/ml polybrene, and incubated in a 37° C. incubator (5% $CO_2$) with occasional stirring for 5 hrs. Fresh medium was then added to maintain the cell density at 5 to $6 \times 10^5$ cells/ml and grown for another 36 to 44 hrs. NIH3T3 was also transduced with 3 ml of viral supernatant in the presence of 8 mg/ml polybrene for 5 hrs followed by the addition of fresh medium. On the following day, the cells were re-fed with fresh medium containing G481 as required. When needed, viral titer was determined in accordance with the Byun et al's method(see: Byun, J. et al., Gene Ther., 3:1018–1020, 1996).

EXAMPLE 1

Defining the Packaging Sequence in MFG

A schematic diagram depicting a retroviral vector MFG (ATCC 68754) is provided in FIG. 1. In MFG, a gene of interest(dotted box) is cloned into the Nco I site containing the start codon, and expressed as a spliced message. MFG contains the 420 bp and 99 bp coding sequences for gag and env, respectively. U3 of MoMLV(Molony murine leukemia virus) is 448 bp long. In FIG. 1, ATG is a start codon of gag, SD is a splice donor site, and SA is a splice acceptor site.

MFG contains gag sequence up to the Nar I site at position #1040 followed by a splice acceptor fragment from the Nde 1 site(#5402) to the Xba 1 site(#5766) in MLV(see: FIG. 1). An adapter oligonucleotide was used to insert an NcoI site at position 7675, converted to a BamH I site, to the end of MLV. The gene inserted at the NcoI site is expressed from a spliced message, resembling the normal spliced env message following MLV infection.

Initially the present inventors were interested in determining whether the gag and env regions of the vector were essentially required for viral functions or not. The former is thought to contain the sequence necessary for viral packaging, whereas the latter does not seem to be needed for any retroviral vector functions. These sequences will enhance the frequency of recombination between the packaging genome and the vector, increasing the possibility of producing RCR. Furthermore, deletion of unnecessary sequences will allow the insertion of larger DNA fragments into the vector.

Figure 2:
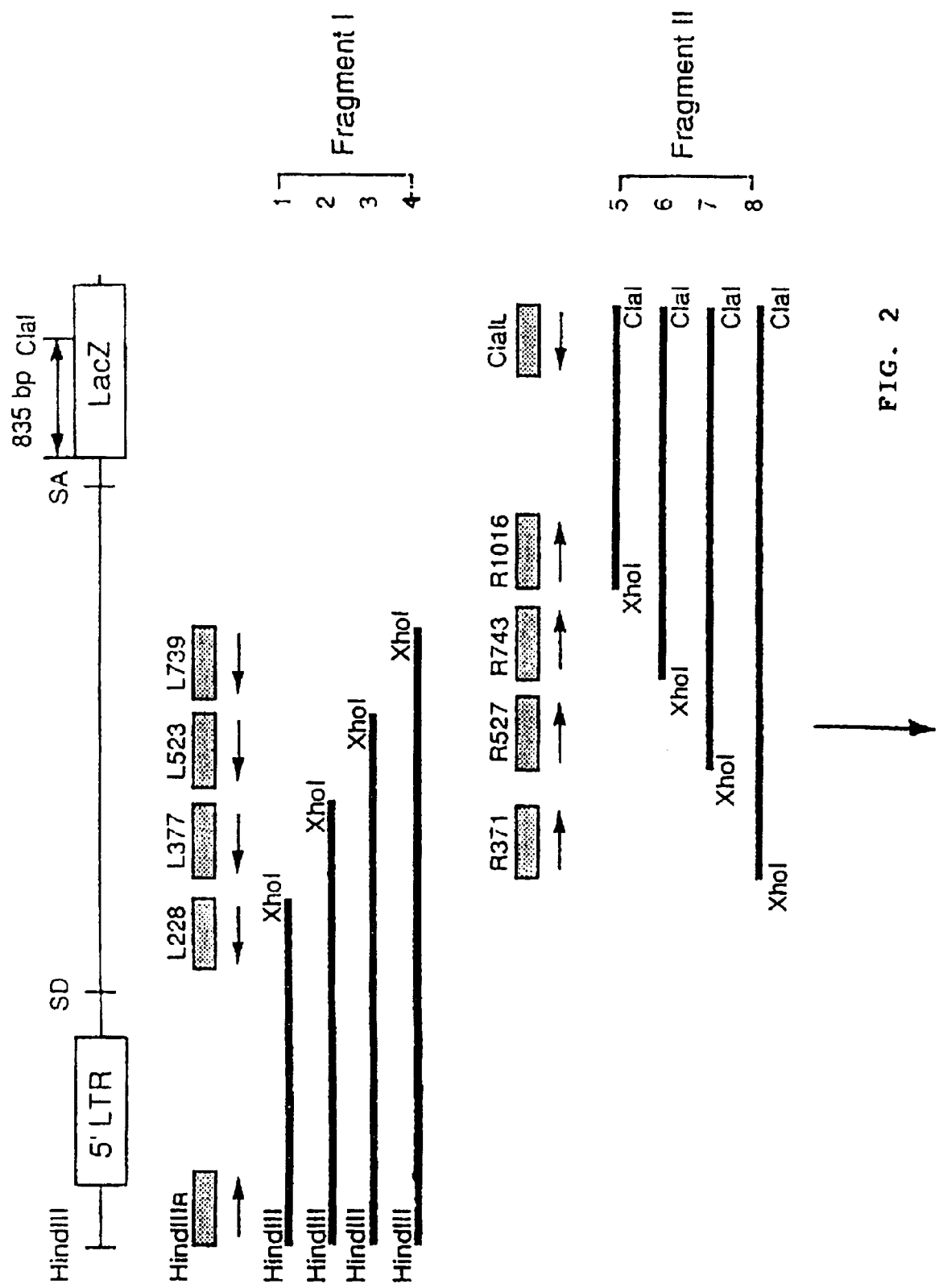
FIG. 2 is a schematic diagram for the construction of vectors containing deletions at the region around the packaging signal sequence.
Figure 2:
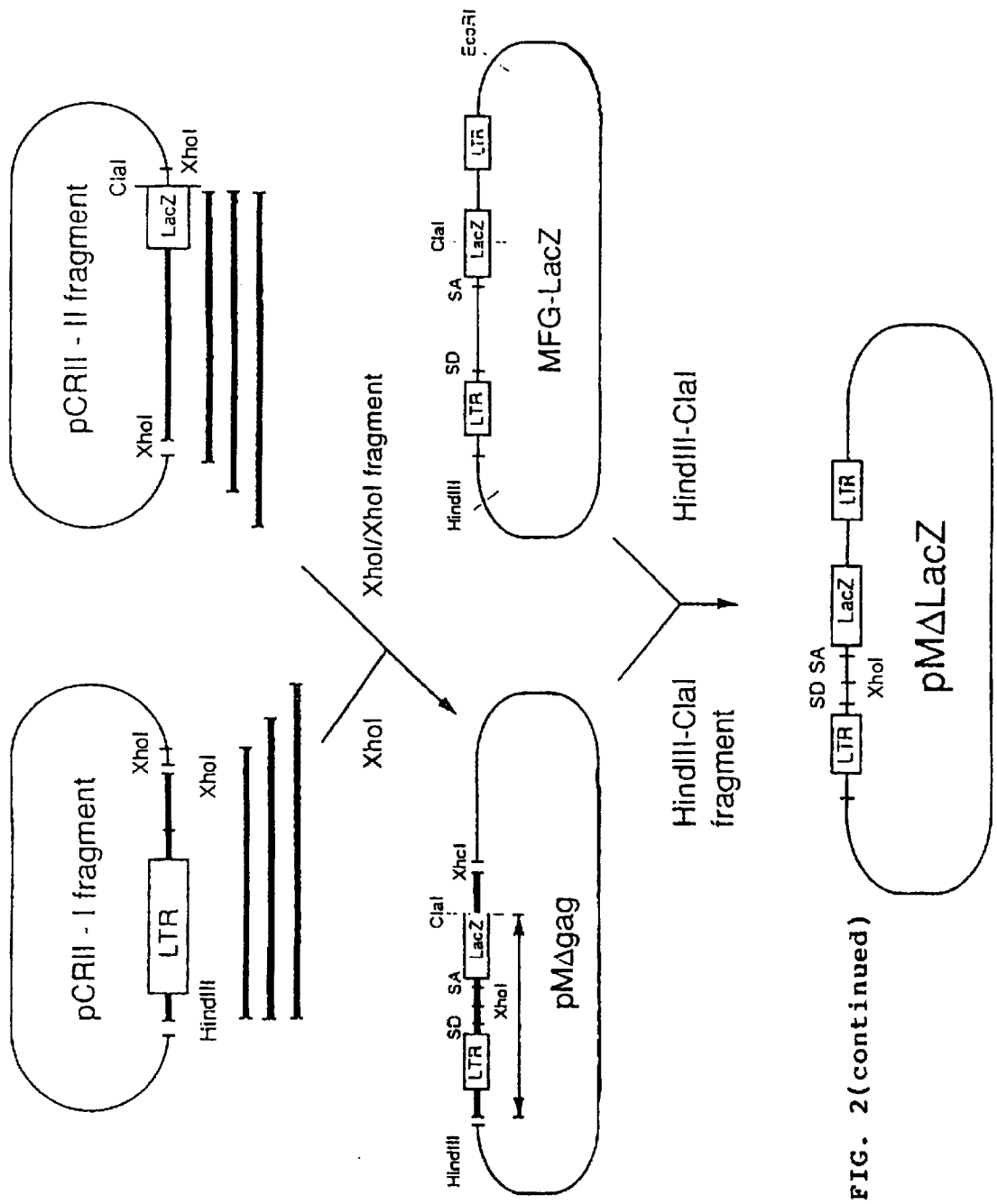

To determine the minimum length of nucleotide sequence required for packaging, a series of deletions between the splice donor and acceptor were generated by polymerase chain reaction(PCR) using proof-reading pfu DNA polymerase(Stratagene, USA) (see: FIG. 2). The nucleotide sequences of final constructs were determined to confirm that there were no mutations introduced by this amplification step.

As can bee seen in FIG. 2, based on MFG-LacZ(see: Bandara, G. et al., Proc. Natl. Acad. Sci., USA, 90:10764–10768, 1993), ten oligonucleotide primers were used for amplification of two types of fragment, Groups I and II. Group I fragments were obtained by PCR using the primer Hind IIIR and one of the four primers L228, L377, L523, and L739. The HindIII linker was attached to Hind IIIR, while the Xho I linker was attached to these L series primers. Group II fragments were generated by PCR using the primer ClaIL and one of the four primers R371, R527, R743, and R1016. The Cla I and Xho I linkers were attached to respective primers. The nuclotide sequence of primers used in this experiment is as follows:

```
HindIIIR SEQUENCE ID NO:1:    GCATTAAAGCTTTGCTCT
                              Hind III L228 SEQUENCE ID NO:2:        GCCTCGAGATAAGTTGCTGGCCAG
                              Xho I L377 SEQUENCE ID NO:3:        GCCTCGAGTCCCTGGGACGTCTCC
                              Xho I L523 SEQUENCE ID NO:4:        GCCTCGAGCAAAAATTCAGACGGA
                              Xho I L739 SEQUENCE ID NO:5:        GCCTCGAGCAGAAGGTAACCCAA
                              Xho I R371 SEQUENCE ID NO:6:        GCCTCGAGGGACTTCGGGGGCCGT
                              Xho I R527 SEQUENCE ID NO:7:        GCCTCGAGGTTTGGGACCGAAGCC
                              Xho I R743 SEQUENCE ID NO:8:        GCCTCGAGAATGGCCAACCTTTAA
                              Xho I R1016 SEQUENCE ID NO:9:       GCCTCGAGCCCTCACTCCTTCTCT
                              Xho I ClaIL SEQUENCE ID NO:10:      ACGCTCATCGATAATTTC
                              Cla I
```

The 8 fragments from Group I and II were amplified and cloned into the plasmid pCR II(Invitrogen, USA), resulting in a series of 4 pCR II-I and 4 pCR II—II constructs. The Xho I-Xho I fragments were isolated from the series of pCR II—II plasmids, and then inserted into the Xho I site of the series of pCR II-I, generating a series of pMAgag constructs. The Hind III-Cla I fragment was isolated from pMAgag and used to replace the Hind III-Cla I fragment(including the 5'LTR) of MFG-LacZ, resulting in a series of pMΔLacZ constructs, now containing deletions between SD and SA. Altogether 9 deletion mutants were constructed, as summarized in FIG. 3, and their effects tested on packaging and transduction efficiencies, using the lacZ gene as a reporter.

Figure 3:
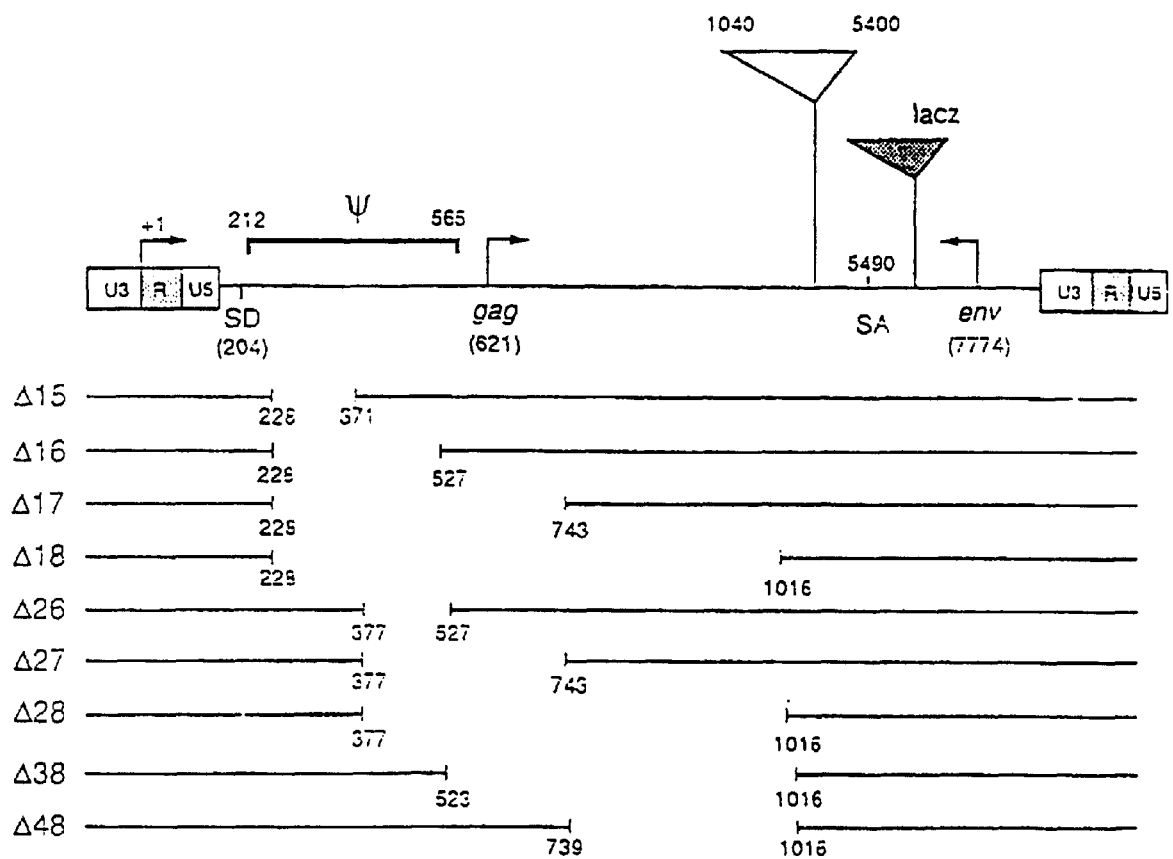
FIG. 3 is a schematic representation of the vectors containing deletions of FIG. 2.

In FIG. 3, ψ indicates the packaging sequence previously defined by Mann et al.(see: Mann et al., Cell, 33:153–159, 1983) which includes the gag coding region as well as the entire sequence between SD and the start codon for gag. The numbering system is based on Shinnick et al's publication (see: Shinnick et al, Nature, 293:543–548, 1981). The region between 1040 and 5400 includes coding sequences for gag and pol and is missing from MFG. LacZ was used as a reporter gene in this study and its relative position is shown as dotted triangle.

Figure 4A:
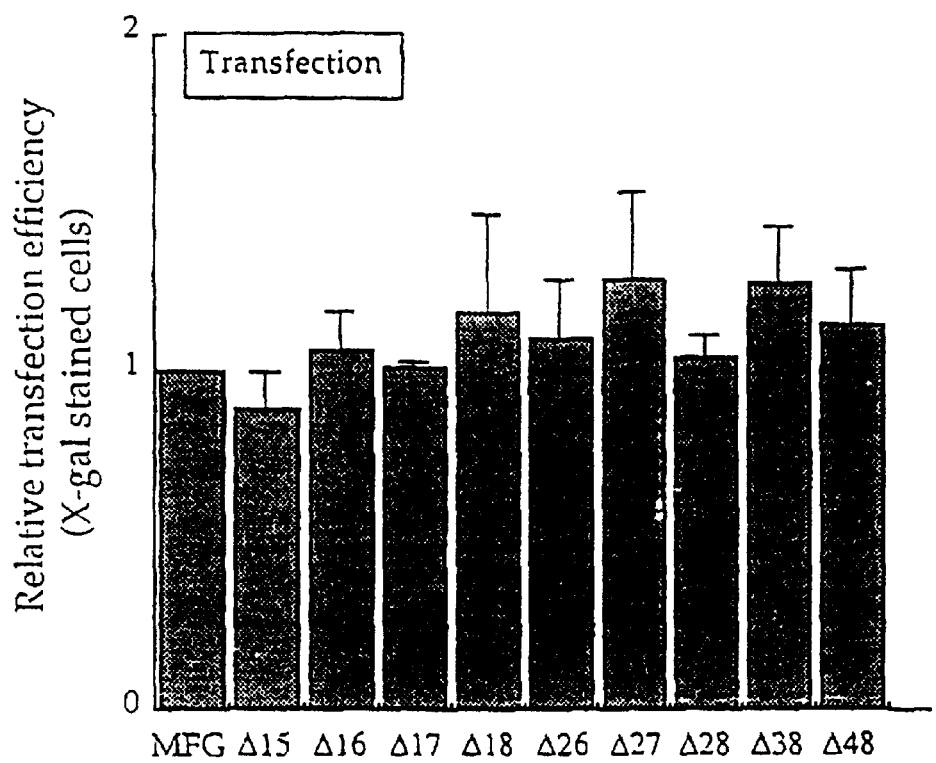
FIG. 4A is a histogram showing effects of deletion on gene expression.

Deletion constructs, together with the parental vector MFG-lacZ, were transfected to the packaging line BING. After 3 days, culture supernatants were filtered through 0.45 μm filters, while cells were stained with X-gal to measure transfection efficiency. Duplicate dishes were also prepared for some constructs and subjected to o-nitrophenyl-β-D-galactopyranoside(ONPG) assay for β-galactosidase activity. X-gal-stained cells were counted to estimate the packaging efficiency(see: FIG. 4A).

Cell-free viral supernatants were used to transduce NIH3T3 cells and after 3 days, cells were stained with X-gal to determine viral titer. Transfection efficiency was determined by measuring both lacZ activity and the number of X-gal stained cells in the transfected packaging line. All mutant constructs gave comparable numbers of blue cells with virtually identical intensity as well as similar levels of lacZ activity, demonstrating that the deletions did not affect gene expression(see: FIG. 43).

Transfection and transduction efficiency of MFG were set to 1 and those of others were normalized to it. More than 5 transfection and transduction experiments were performed at separate times. In one independent experiment, 4 to 6 transfection and transduction experiments were carried for each mutant.

Figure 4B:
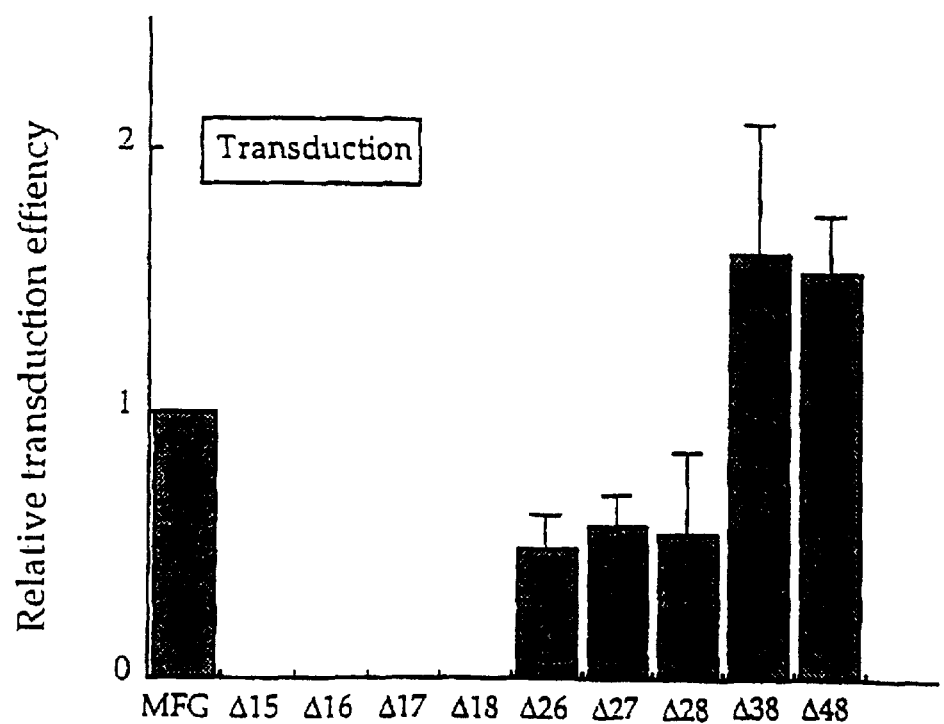
FIG. 4B is a histogram showing effects of deletion on viral titers.

The relative titers of each of the deletion constructs is shown in FIG. 4B. The deletion constructs can be divided into three classes, depending on their effects on packaging efficiency. First, four mutant constructs containing the deletion from 228 to 371 (Δ15, Δ16, Δ17, Δ18) completely lost the packaging function. Secondly, the sequence from 377 to 527 appeared to be necessary, but not essential, for the optimal packaging efficiency since the titers of these mutant constructs (Δ26, Δ27, Δ28) were consistently lower than control. Thirdly, there are two mutant constructs that reproducibly showed a maximally 2-fold increase in packaging efficiency. The mutant construct Δ38, which always gave the highest titer, contains a 500 bp deletion removing the entire gag coding sequence present in MFG.

The mutational analysis of the packaging signal produced the three types of phenotype(no packaging, decreased packaging, and increased packaging) and defined at least 3 regions involved in packaging. The first group of mutants, all of which contained a deletion in Region A (#228 to #371) showed absolutely no packaging function, is consistent with previous reports(see: Mann, R. et al., Cell, 33:153–159, 1983; Mann, R., and D. Baltimore., J. Virol., 54:401–407, 1985; Alford, R. L. et al., Virology, 183:611–619, 1991). The second phenotype is characterized by 2 fold decrease in packaging, localizing the region that are not essential but necessary for the maximum packaging function. The third group of deletion mutants, Δ38 and Δ48, reproducibly showed maximally 2-fold higher packaging efficiency than the parental type, suggesting the possible presence of the sequence interfering with the packaging function, probably at the 739 to 1016 region (Region C). In mutant Δ38 which contains almost a 500 bp deletion, the entire gag coding sequence was removed, but showed no decrease in packaging efficiency. However, when deletion is extended to 377 (Region B) as in Δ28, packaging efficiency was decreased substantially.

In summary, there seems to be a complex array of sequences that are involved in viral packaging; Region A essential for viral packaging, Regions B which is necessary, but not essential, for optimal packaging, and Region C which probably interferes with packaging. When both Regions B and C were deleted, the B phenotype was shown. These results show that the entire N-terminal gag sequence is not necessary for efficient viral packaging in the context of the MFG vector. The retroviral vector lacking the gag coding region produced viral titer and levels of gene expression similar to the one containing this sequence even when various reporter genes including CAT, EPO and GM-CSF were used, as shown in Examples later.

EXAMPLE 2

Deletion of the Residual Env Sequence

Figure 6A:
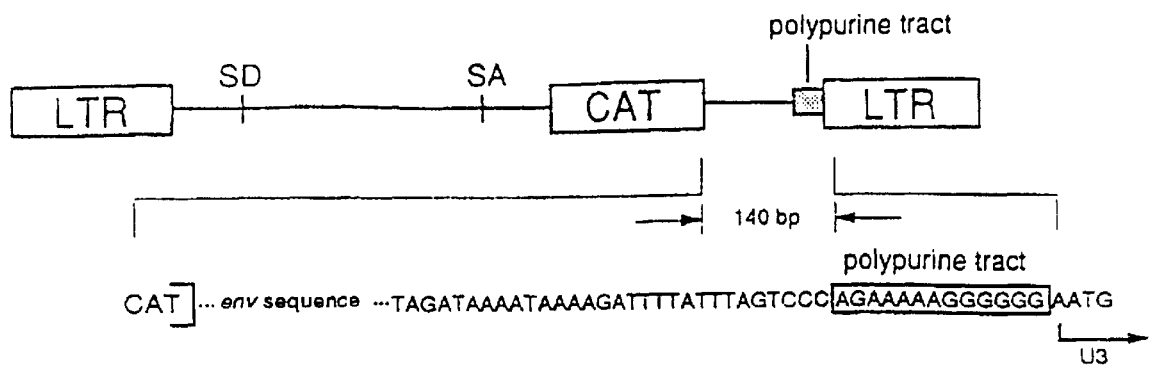
FIG. 6A is a schematic representation of the vector in which the residual env coding sequence is deleted.
Figure 6A:
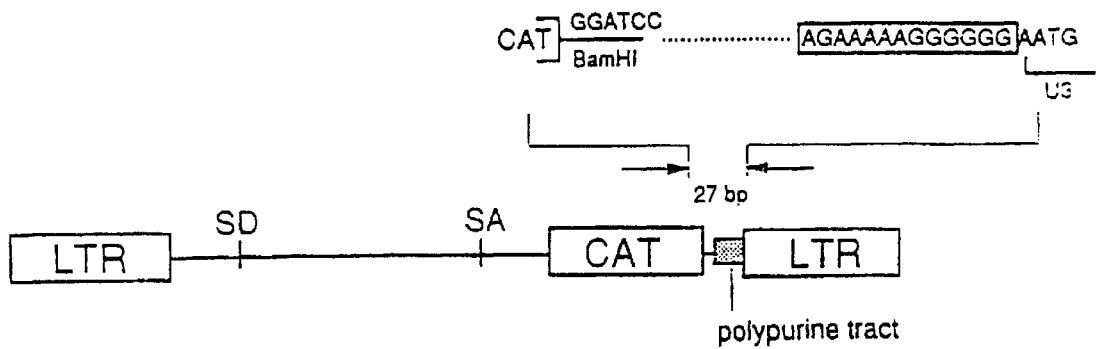

MFG also has approximately 140 bp between the stop codon of the foreign gene and the 5'end of U3(see: FIG. 1 and FIG. 6A). This region contains the 99 bp env coding sequence which can be used as a template for recombination with the same sequence in the packaging line. We deleted 113 bp, including the entire residual env coding sequence, but left the polypurine tract intact(see: FIG. 6A).

Figure 5:
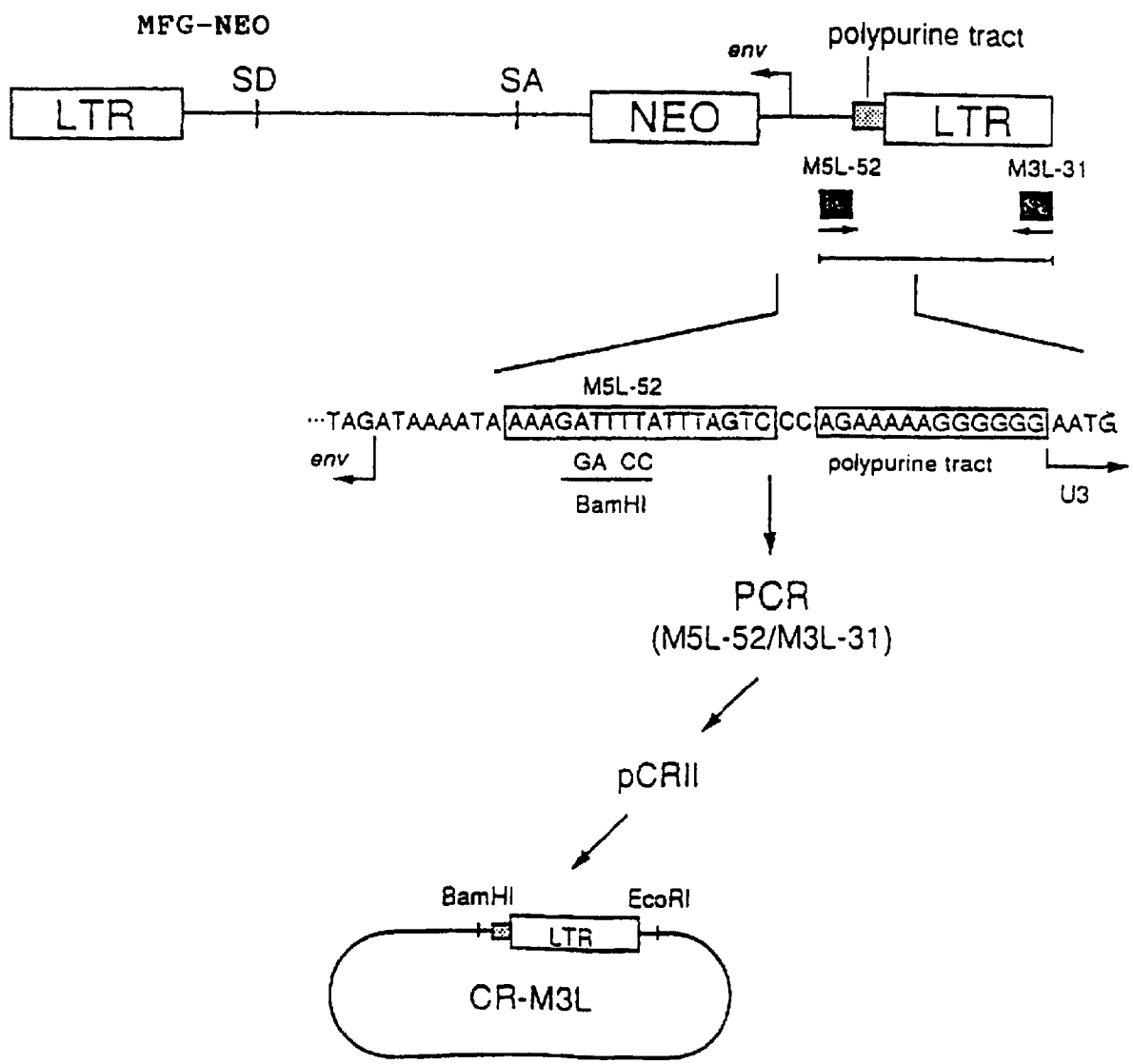
FIG. 5 is a schematic diagram for the construction of a vector in which a residual env coding sequence is deleted.
Figure 5:
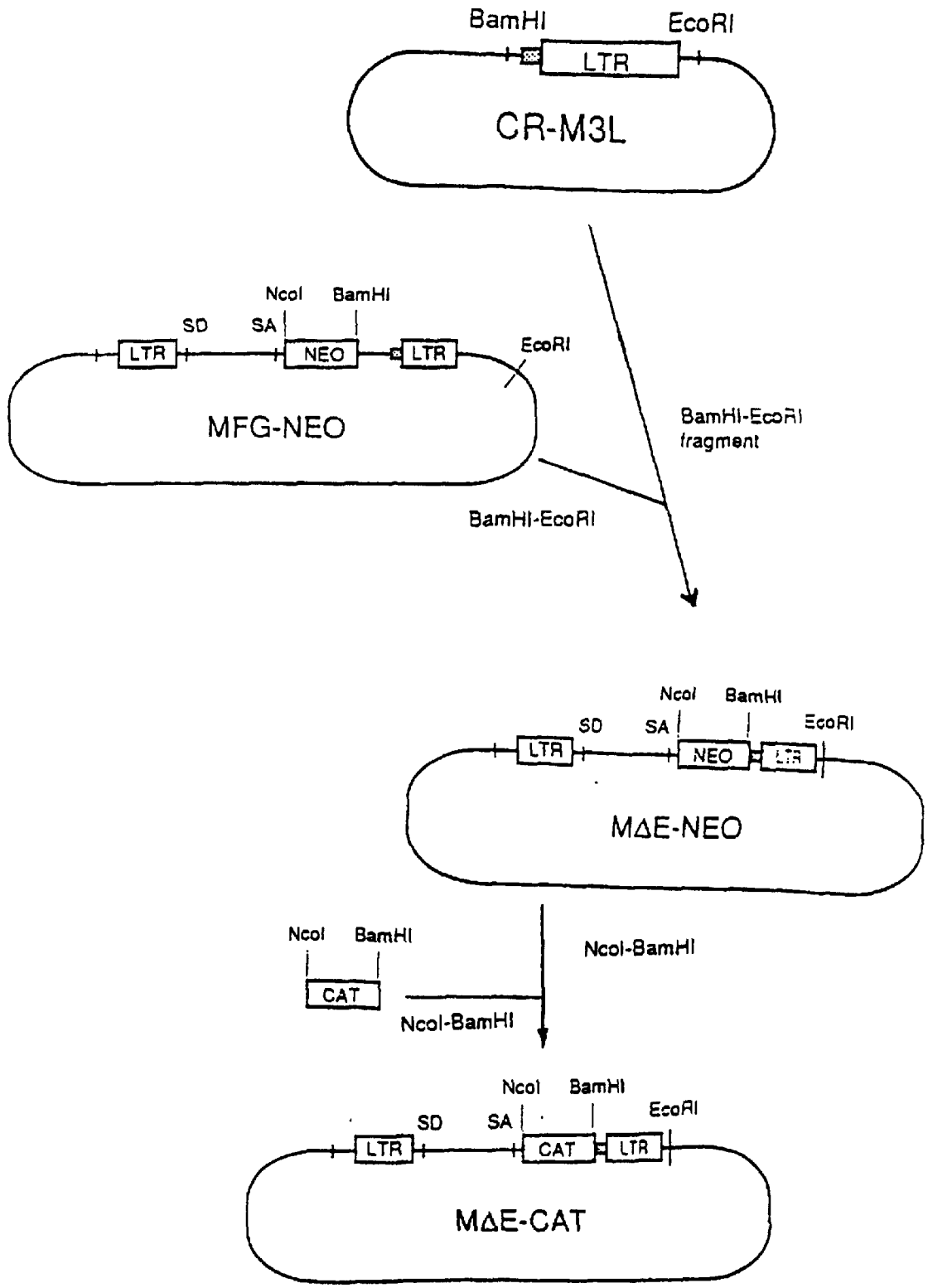

To remove the residual env sequences, the PCR was performed with MFG-NEO(see: Byun, et al., Gene Ther., 3:780–788, 1996) using the primers M3L-52 and M3L-3l, as illustrated in FIG. 5. Underlined are restriction linkers attached to each primer.

```
M3L-52              AAAGGATCCATTTAGTCT
SEQUENCE ID NO:11:     BamHI

M3L-31              GAATTCATGTGAAAGGCGGCCGCTGA
SEQUENCE ID NO:12:     EcoR I
```

The amplified product covered the polypurine tract and the entire 3'LTR. The amplified fragment was then cloned back into pCR II, resulting in CR-M3L. The BamH I-EcoR I fragment from CR-M3L replaced the same BamH I-EcoR I fragment of MFG-NEO, generating MΔE-NEO. The Nco I-BamH I Neo gene was replaced with the Nco I-EamH I CAT sequence from MFG-CAT(see: Byun, J. et al., Gene Ther., 3:780–788, 1996), resulting in MΔE-CAT.

To allow comparison of the levels of gene expression, the bacterial CAT gene was used as a reporter(MFG-CAT, MΔE-CAT). CAT assays were performed by standard procedures as previously described by Byun et al's publication (see: Byun, J. et al., Gene Ther., 3:780–788, 1996). Two days after transfection or transduction, cells were harvested, washed once with PBS, and resuspended in 0.25M Tris-HCl (pH 7.5). Total proteins were prepared by 4 to 5 cycles of freeze-thaw followed by incubation at 65° C. for 7 min. Equivalent amounts of protein were assayed for CAT activity. The percent conversion of C-chloramphenicol to its acetylated forms was determined by quantiating the intensity of each spot with a phosphoimager(FUJIX BAS 1000).

Figure 6B:
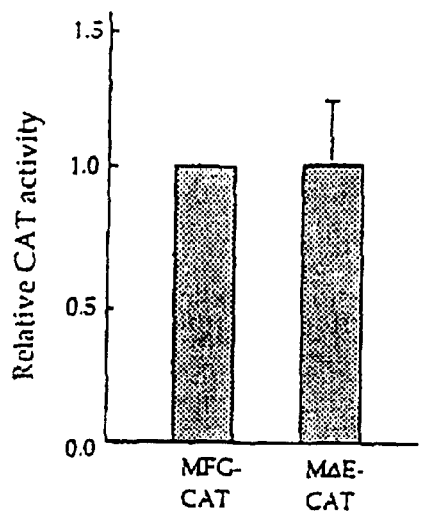
FIG. 6B is a histogram showing CAT(chloramphenicol acetyltransferase) activity of CRIP packaging cells transfected with MΔE-CAT plasmid.
Figure 6C:
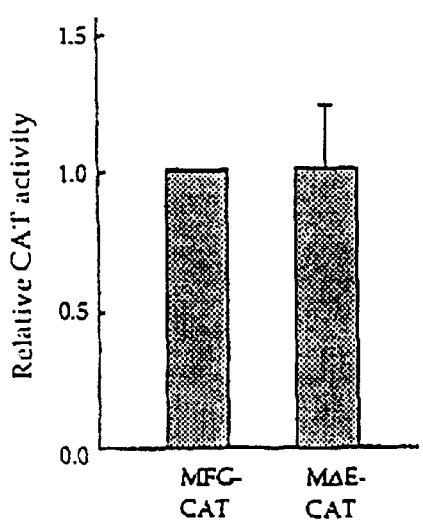
FIG. 6C is a histogram showing CAT activity of human promonocytic cell line U937 transducted with cell-free viral supernatants obtained from the transfected packaging cells of FIG. 6B.
Figure 6D:
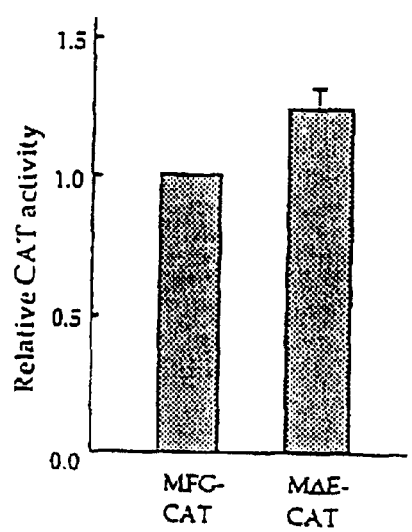
FIG. 6D is a histogram showing CAT activity of T lymphoid cell line CEM transducted with cell-free viral supernatants obtained from the transfected packaging cells of FIG. 6B.

MFG-CAT and MΔE-CAT constructs were transfected to the packaging line CRIP, cell-free viral supernatants were used to transduce the human promonocytic line U937 and T lymphoid line CEM-SS, followed by CAT assay(see: FIGS. 6B, 6C and 6D). In FIG. 6B, expression of MFG were set to 1, MΔE-CAT always produced levels of CAT activity similar to MFG-CAT in both transfected packaging lines and transduced target cells, suggesting that deletion of residual env sequences did not significantly affect gene expression.

EXAMPLE 3

Deletion of the LTR U3 Sequence

Figure 7:
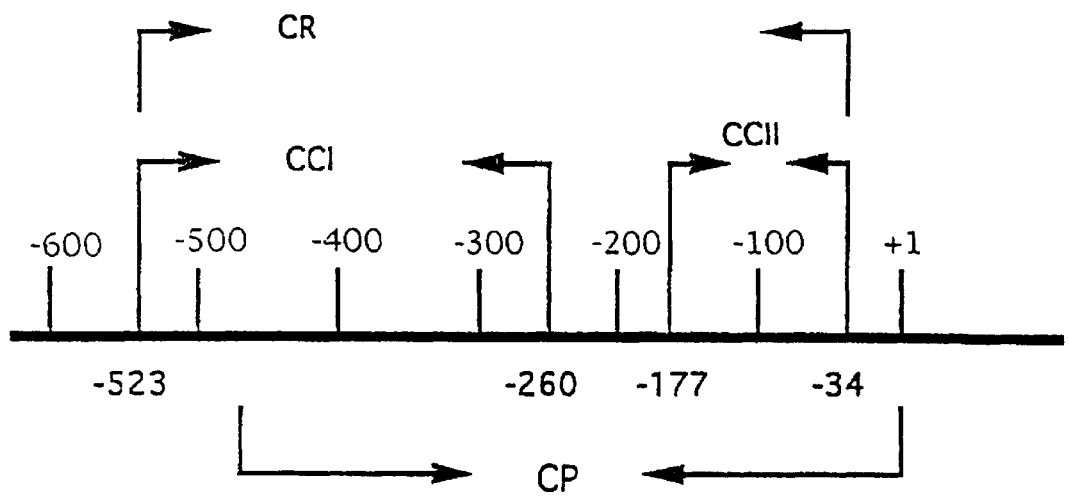
FIG. 7 is a schematic representation on four fragments from the major immediate-early promoter of human cytomegalovirus, which are to be used to substitue the U3 sequence.
Figure 7:
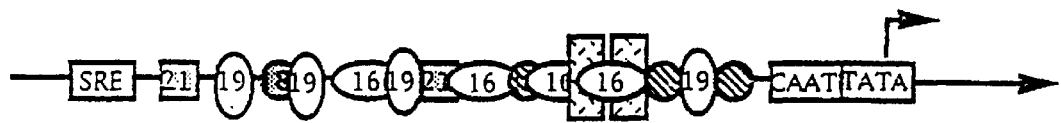
Figure 10:
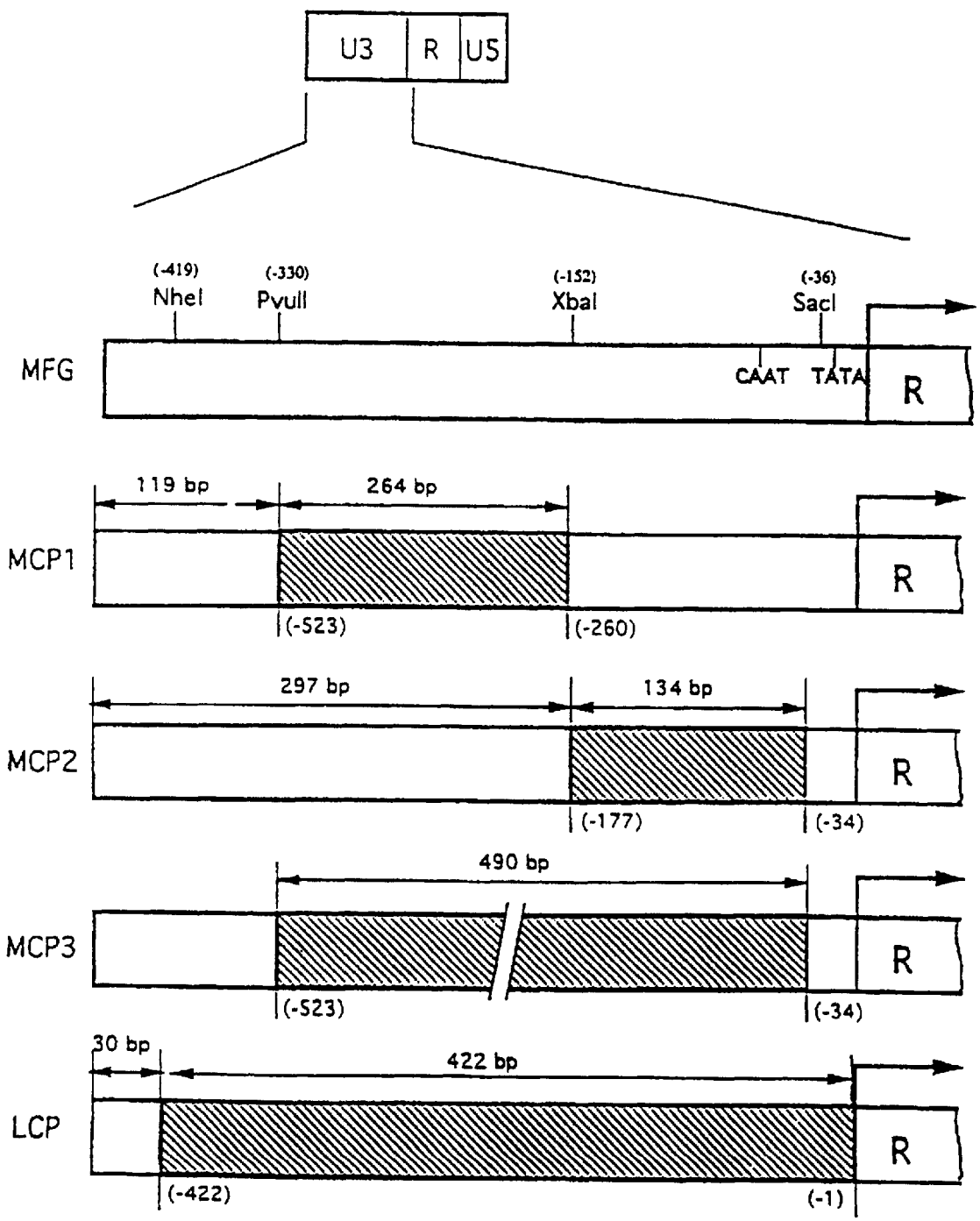
FIG. 10 is a schematic diagram of chimeric LTRs.

To test whether the nucleotide sequence present in the LTR is essential for viral function other than as a promoter and also whether the LTR could be substituted with a heterologous promoter sequence, the inventors constructed four hybrid LTRs in which retroviral sequences were deleted and replaced with heterologous promoter fragments of similar lengths. As a model system, the inventors isolated the four fragments from the major immediate-early promoter (MIEP) of human cytomegalovirus (HCMV) which contains sequences interacting with various cellular transcription factors such as NF-kB, ATF, and AP1 (see: FIG. 7). Various lengths of U3 were deleted and four fragments from MIEP, called CR, CCI, CCII and CP, then added to respective sites(see: FIG. 10).

Figure 8:
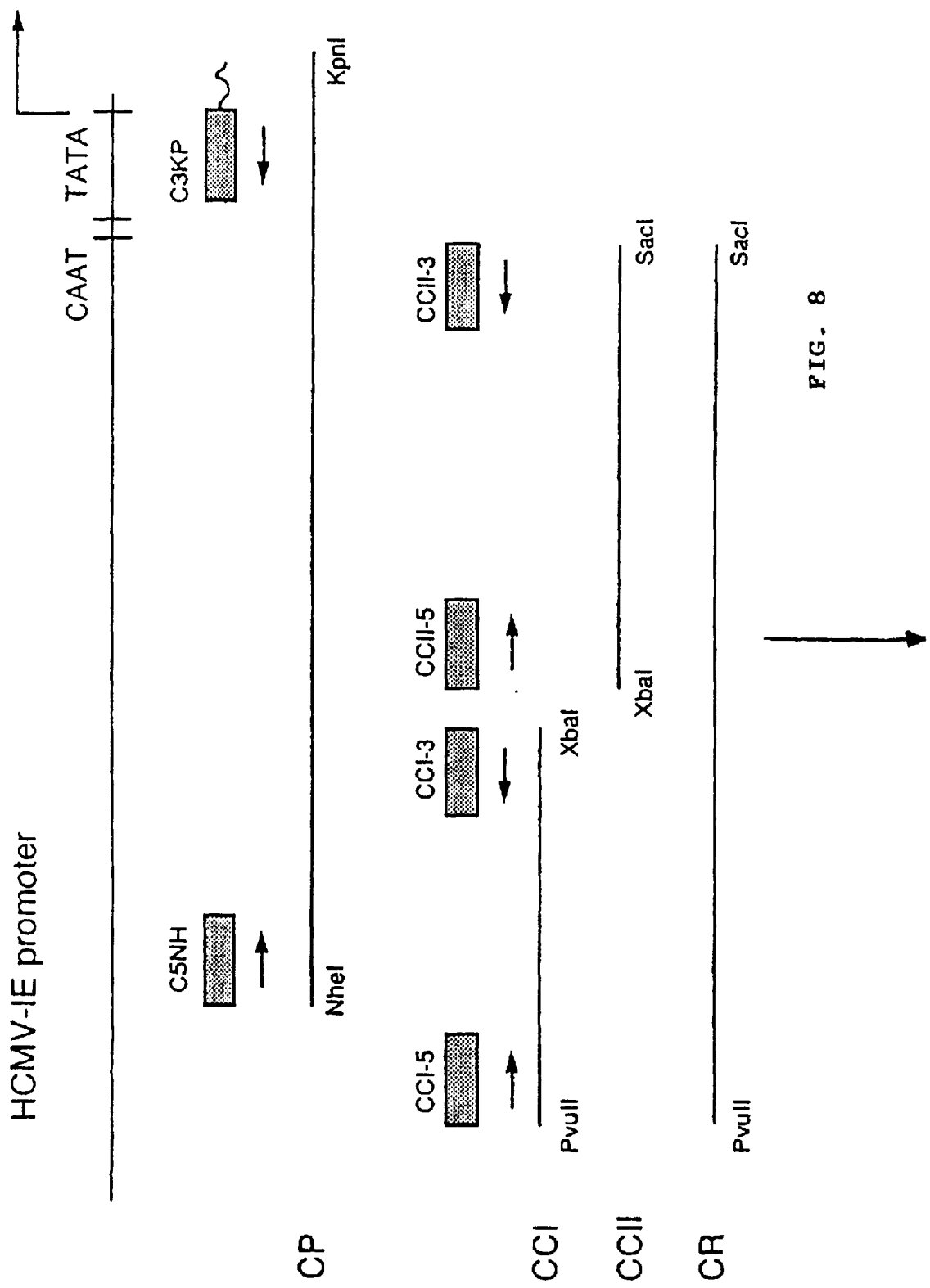
FIG. 8 is a schematic diagram for the construction of vectors containing four fragments of FIG. 7.
Figure 8:
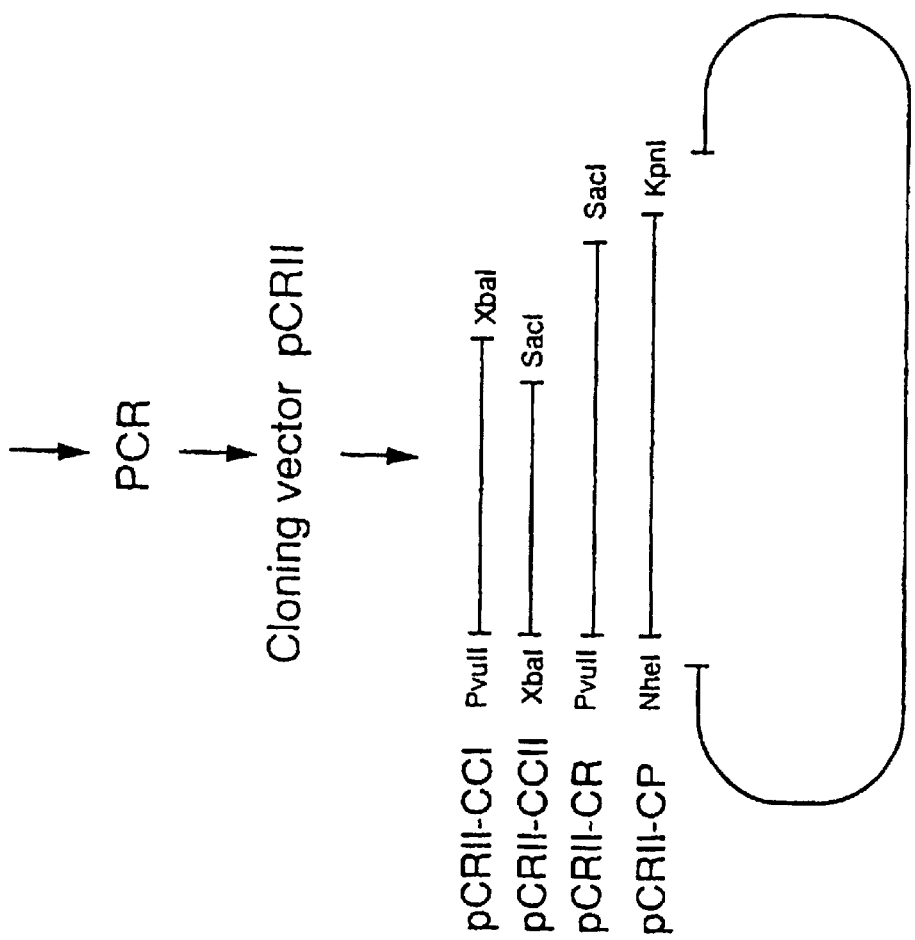

The chimeric promoters containing the HCMV IE promoter elements in the MLV LTR were constructed as follows: First, four HCMV IE promoter elements were amplified by PCR using 6 primers as shown in FIG. 8, and cloned into the plasmid pCR II. To 5' and 3' ends of each primer, restriction sites that are naturally present in the U3 of MLV were added as indicated. The nucleotide sequences of these primers are:

```
C5NH SEQUENCE ID NO:12:    GCTAGCGGGACTTTCCATTGACGT
                             Nhe I

C3KP SEQUENCE ID NO:13:    GGGTACCCGGGCGACTCAGTCAATCGGAGGAGGA
                             Kpn I

CCI-5 SEQUENCE ID NO:14:   CGATCGCCGCGTTACATAAC
                             Pvu II

CCI-3 SEQUENCE ID NO:15:   TCTAGAGGAAACTCCCGTAAG
                             Xba I
```

-continued

```
CCII-5 SEQUENCE ID NO:16:  TCTAGAGGTTTGACTCACGG
                           Xba I

CCII-3 SEQUENCE ID NO:17:  GAGCTCCCTACCGCCCATTT
                           Sac I
```

Figure 9:
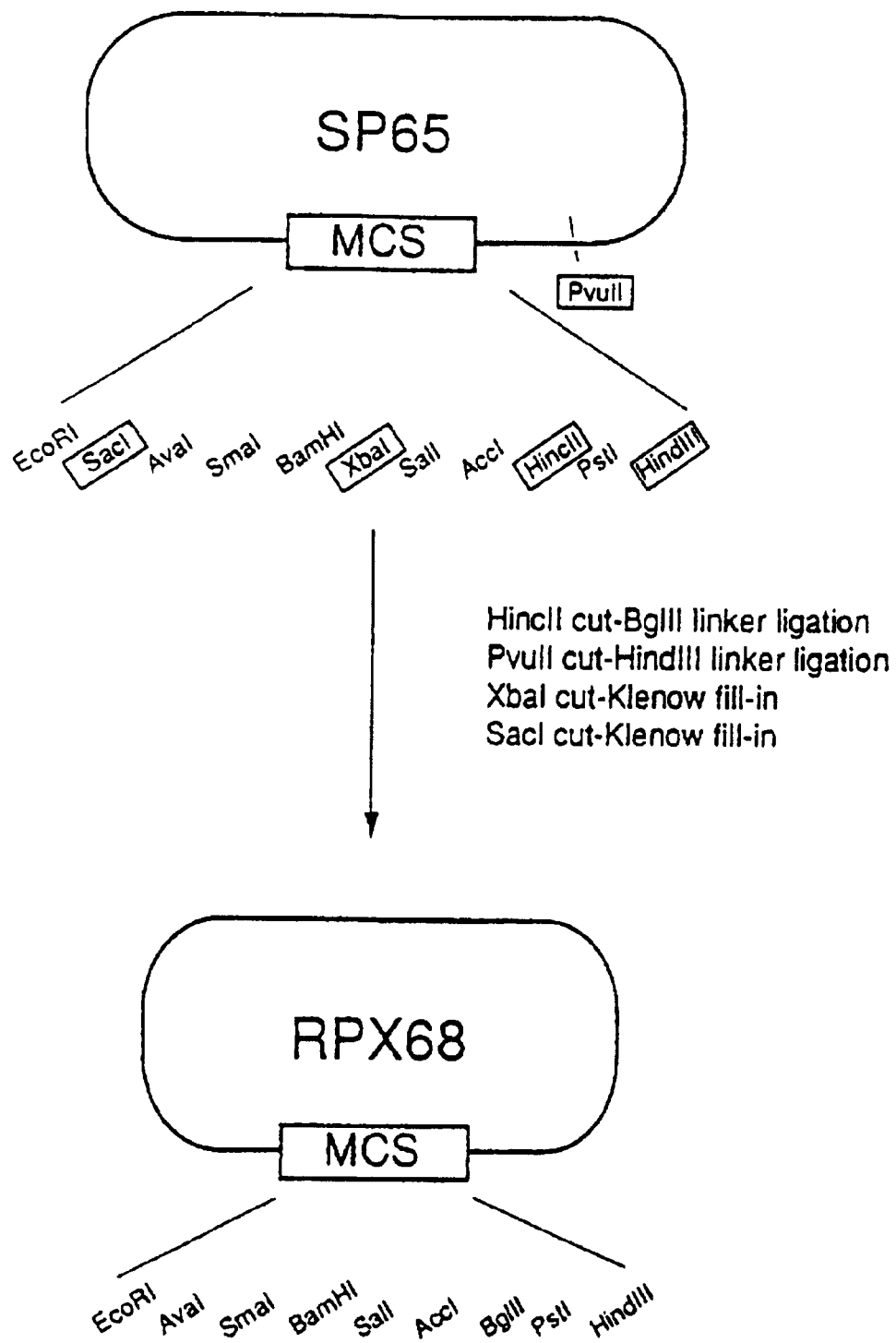
FIG. 9 is a schematic diagram for the construction of a cloning vector RPX68.
Figure 11:
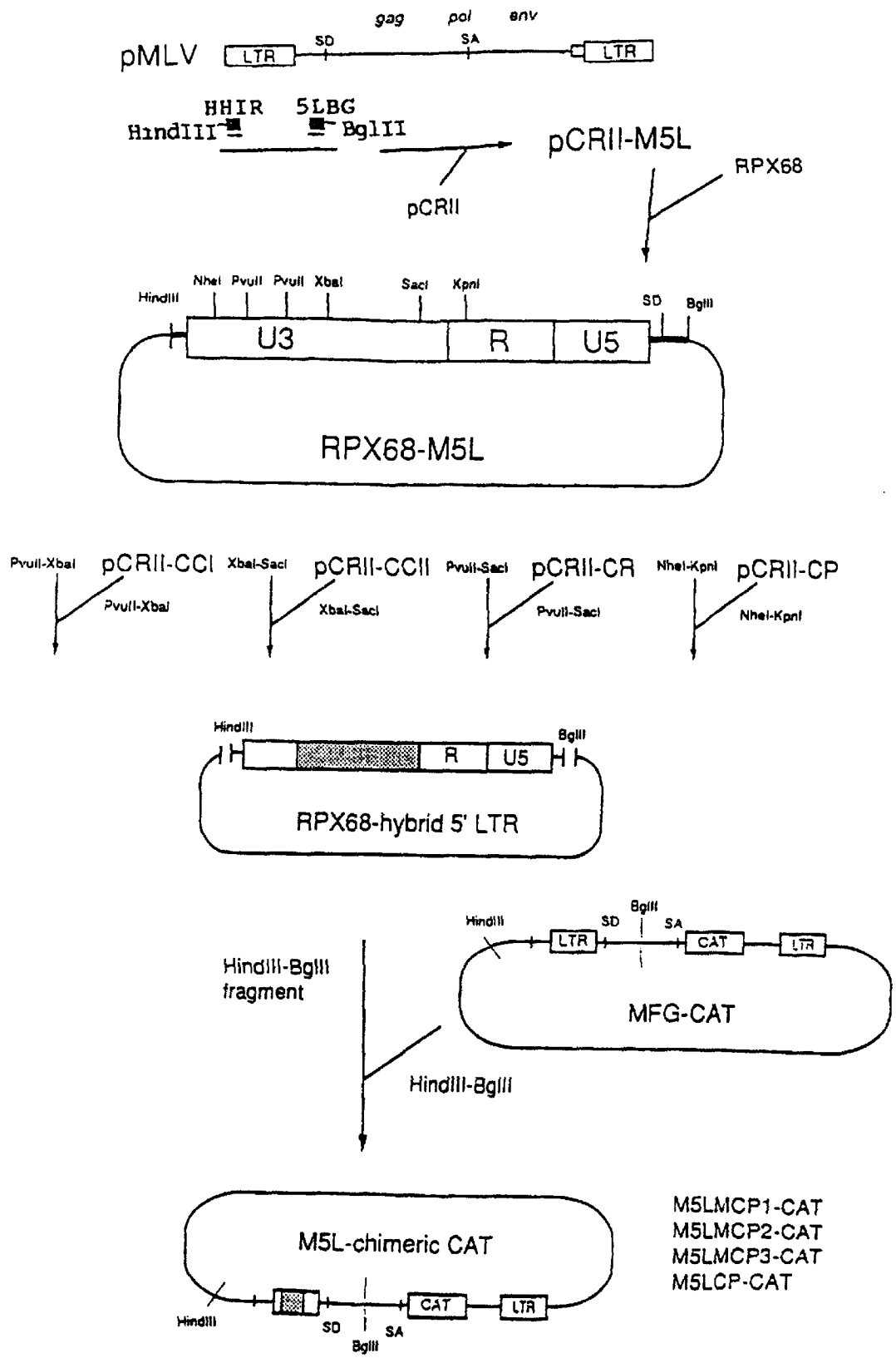
FIG. 11 is a schematic diagram for the construction of retroviral vectors containing hybrid U3 at the 5'LTR.

Secondly, the cloning vector SP65(Promega, USA) was changed to RPX68, by removing the region between Hind III and Pvu II, leaving Hind III intact and filling-in with Xba I and Sac I sites, for the convenience of further manipulation, as illustrated in FIG. 9. Thirdly, the plasmid RPX68-M5L, the RPX68 containing the entire 5'LTR of MLV, was constructed by amplifying the same region from pMLV(see: Shinnick, T. M. et al., Nature 293:543–548, 1981), as shown in FIG. 11. The nucleotide of primers used in amplifying 5'LTR of MLV are:

```
HHIR SEQUENCE ID NO:18:   AAGCTTATGTGAAAGACCCCTCCTG
                          Hind III 5LBG (SEQ ID NO:20:       AGATCTGGCGCCTAGAGAAGG
                          Bgl II
```

RPX68-M5L was subjected to four different restriction digestions. Each restriction site used in digestions is unique, and they all cut the sites inside the 5'LTR. Four HCMV IE promoter fragments were then isolated from the pCRII constructs containing these fragments(pCRII-CCI, pCRII-CCII, pCRII-CR, and pCRII-CP), and then used to substitute the PvuII-XbaI, XbaI-SacI, PvuII-SacI, and NheI-KpnI fragments of the LTR, generating four plasmids (RPX68-hybrid 5'LTR). The Hind III-Bgl II fragment of MFG-CAT containing the 5'LTR, results in four M5L-chimeric CAT plasmids; M5LMCP1-CAT, M5LMCP2-CAT, M5LMCP3-CAT and M5LCP-CAT. The chimeric promoters constructed this way are summarized in FIG. 10.

Four restriction sites(NheI, PvuII, XbaI, and SacI) shown in FIG. 10 are naturally present in U3 and their coordinates are shown in parentheses. These sites were used to clone the four HCMV MIEP fragments. The relative position of CAAT and TATA boxes of U33 are indicated. The numbers shown above the LTR are the lengths of U3 (unshaded) or HCMV MIEP(shaded) that replaced a part of U3, while those in parentheses are the coordinates of MLV based on Shinnick et alls publication(see: Shinnick, T. M. et al., Nature 293:543–548, 1981).

MCP1 contains the 264 bp HCMV IE promoter fragments in the region between ~330 (PvuII) and –152 (XbaI) of U3. In MCP2, 117 bp of U3(XbaI-SacI) was replaced with the 144 bp MIEP promoter. In MCP3, the U3 region from –330 (PvuII) to –36 (SacII) was substituted with the 490 bp HCMV promoter. In MCP2 and MCP3, the retroviral TATA box, but not the CAAT sequence, is intact. LCP has the 422 bp HCMV promoter which contains full promoter activity.

where gene expression is essentially under the control of the HCMV IE promoter.

Figure 12:
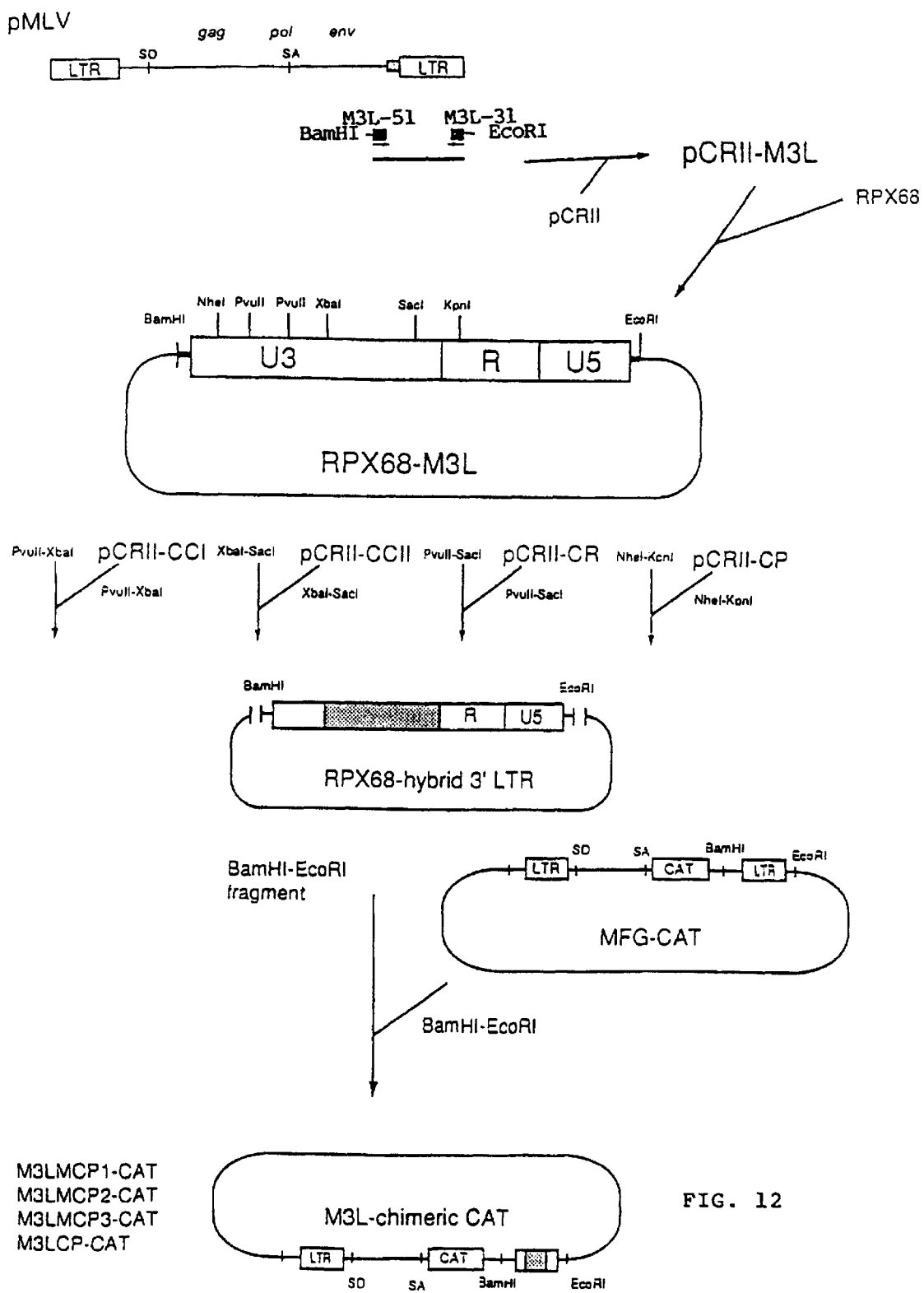
FIG. 12 is a schematic diagram for the construction of retroviral vectors containing hybrid U3 at the 3'LTR.

The original 3'LTR in MFG-CAT was then replaced with these hybrid LTRs as shown in FIG. 12. To insert the HCMV IE promoter fragments to the 3'LTR, RPX68-M3L was first constructed by amplifying the 3'LTR from pMLV and cloning it into RPX68 as shown in FIG. 12. The oligonucleotide primers used in this amplification are M3L-51 and M3L-31 with the latter used to construct MΔE-CAT. The nucleotide sequence of M3L-51 is:

```
M3L-51 SEQUENCE ID NO:21:  AAAGGATCCGATTAGTCCAATTTG
                           BamH I
```

Figure 13A:
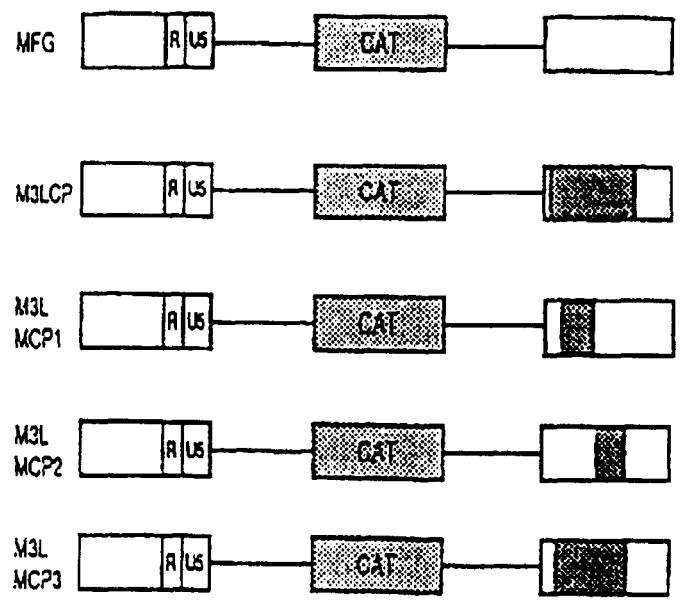
FIG. 13A is a schematic representation of 4 retroviral vectors containing hybrid U3 at the 3'LTR.

As in the case of RPX68-M5L, RPX68-M3L was subjected to 4 different restriction digestions and the retroviral LTR fragments were replaced with 4 HCMV IE promoter fragments to generate RPX68-hybrid 3'LTR in the same manner as for RPX68-hybrid 5'LTR. The 4 BamH I-EcoR I fragments from RPX68-hybrid 3'LTR were then used to substitute the BamH I-EcoR I fragment containing 3'LTR of MFG-CAT, resulting in four M3L-chimeric CAT plasmids; M3LMCP1-CAT, M3LMCP2-CAT, M3LMCP3-CAT, and M3LCP-CAT(see: FIG. 13A).

Figure 13B:
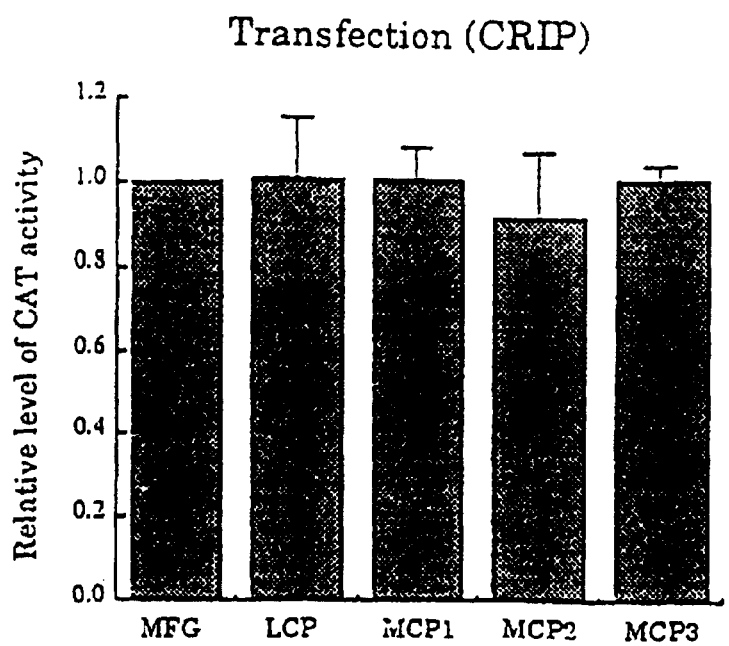
FIG. 13B is a histogram showing CAT activity of CRIP packaging cells transfected with retroviral vectors of FIG. 13A.
Figure 13C:
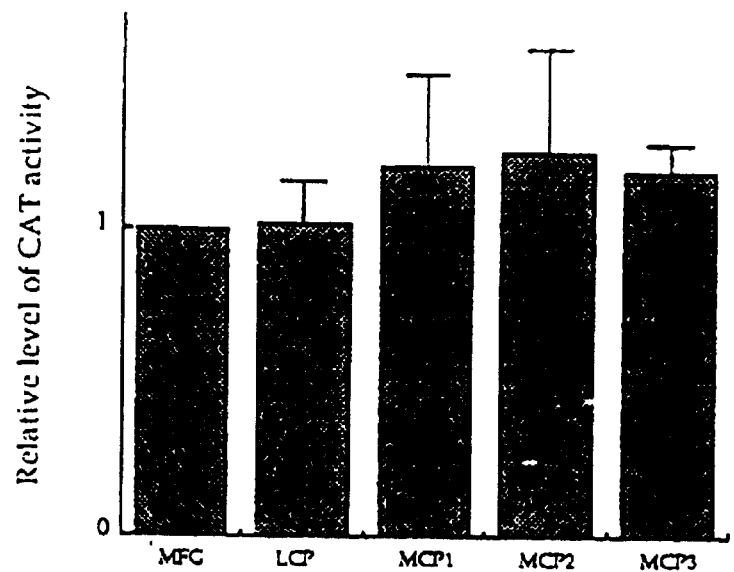
FIG. 13C is a histogram showing CAT activity of cell line NIH3T3 transducted with cell-free viral supernatants obtained from the transfected packaging cells of FIG. 13B.
Figure 13D:
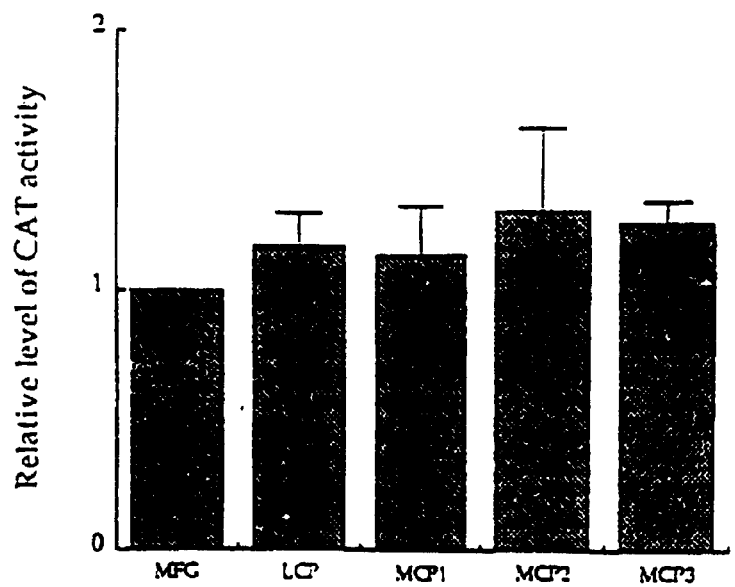
FIG. 13D is a histogram showing CAT activity of H9 cells transducted with cell-free viral supernatants obtained from the transfected packaging cells of FIG. 13B.

The four CAT constructs containing hybrid promoters in the 3'LTR, together with the parental vector MFG-CAT, were transfected to CRIP cells and cell-free supernatants used to transduce various human cell lines. The level of CAT activity was measured after either transfection of the packaging line or transduction of various cell lines. Since all constructs have the MLV LTR at 5' end in transfected cells, levels of CAT activity in transfected CRIP cells were always comparable(see: FIG. 13B). The level of CAT activity was also quite similar following transduction of NIH3T3 and the human Tlymphoid H9 cells(see: FIGS. 13C and 13D).

Figure 14:
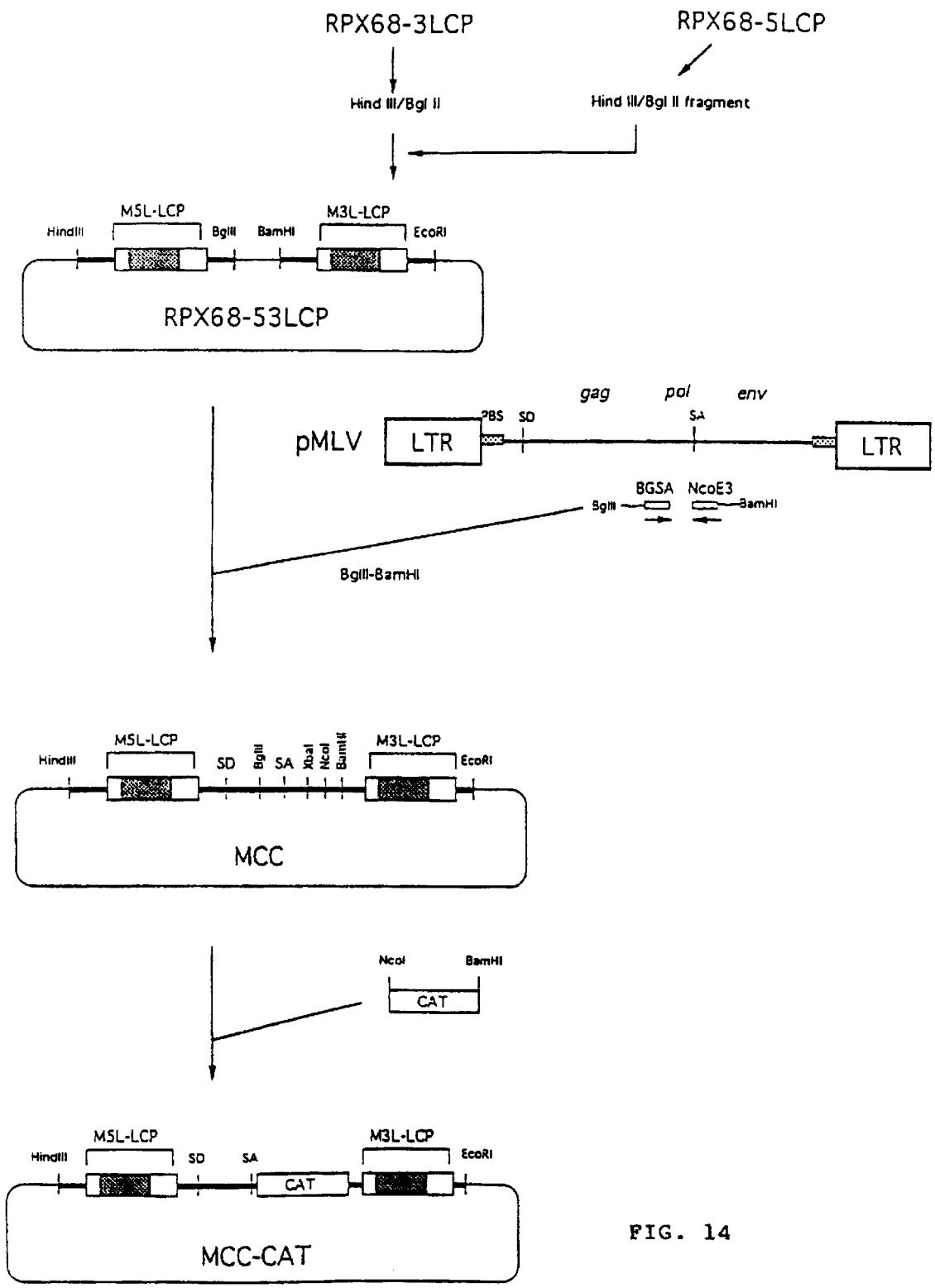
FIG. 14 is a schematic diagram for the construction of a retroviral vector containing hybrid U3 at both 5' and 3'LTRs.

To further demonstrate that the U3 sequence deleted in the above experiment is not required for viral replication or gene expression, the present inventors next inserted a hybrid LTR at both 5' and 3' ends(see: FIG. 14). In this particular examples the inventors used the hybrid LCP LTR containing the largest deletion and insertion. To construct MCC-CAT containing the hybrid promoter at both 5' and 3'LTR, RPX68-53LCP was constructed by inserting the Hind III-Bgl II fragment from RPX68-M5LCP into the Hind III-Bgl II site of RPX68-M3LCP as illustrated in FIG. 14. To provide SA and Nco I at the start codon of the env gene, pMLV was amplified by PCR using the primer BGSA and NcoE3.

```
BGSA SEQUENCE ID NO:22:  ATGAGATCTTATATGGGGCACC
                            Bgl II

NcoE3 SEQUENCE ID NO:23: GGATCCGGCCATGGCTGTCTAGAGGATGGTCCTCCCCCGG
                         BamH I   Nco I    Xba I
```

In this construct, the entire U3 except for 30 bp present at the 5 end was deleted from the hybrid LTR, resulting in an LTR The amplified Bgl II-BamH I product was cloned into the Bgl II/BamH I site of RPX68-53LCP, generating MCC.

Finally, the Nco I-BamH I CAT cassette was inserted into Nco I/BamH I sites of MCC, resulting in MCC-CAT(see: FIG. 14).

CRIP cells were transfected with MCC-CAT and MFG-CAT, and cell-free viral supernatants used to transduce a variety of cell lines. One representative result is shown in Table 1. For each cell line, expression of MFG-CAT was set to 1 and that of MCC-CAT normalized to it. Because assay conditions were different among various cell lines, direct comparison between cell lines based on the above numbers should be avoided. Transductions were performed at least 3 to 5 times for each line.

TABLE 1

| Vector Cell Line | MFG-CAT | MCC-CAT |
| --- | --- | --- |
| NIH3T3 | 1 | 1.18 ± 0.21 |
| U937 | 1 | 1.75 ± 0.80 |
| H9 | 1 | 0.75 ± 0.00 |
| CEM-SS | 1 | 1.16 ± 0.11 |

As shown in Table 1, MCC always produced levels of CAT activity similar to the parental vector, following transduction of NIH3T3, U937, H9 and CEM-SS cell lines, suggesting that almost all the U3 sequence could be deleted from both 5' and 3'LTRs without any deleterious effects on retroviral functions.

EXAMPLE 4

Expression of the Two Genes by a Single Transcriptional Unit

The original version of MFG does not contain the selectable marker. However, expression of more than one gene would make a retroviral vector more versatile in its application to various in vitro experiments or gene therapy trials. It has been reported that IRES elements can be inserted into MFG, allowing for expression of multiple genes from a single polycistronic message(see: Zitvogel, L. et al., Hum. Gene Ther., 5:1493–1506, 1994; Morgan, R. A., Nucleic Acids Res., 20:1293–1229, 1992; Byun et al., Gene Ther., 3:780–788, 1996). In the following example, the inventors tested the efficiency of gene expression in EMCV IRES-containing retroviral vectors also harboring modifications within the gag, env and both 5' and 3'LTRs.

Figure 15:
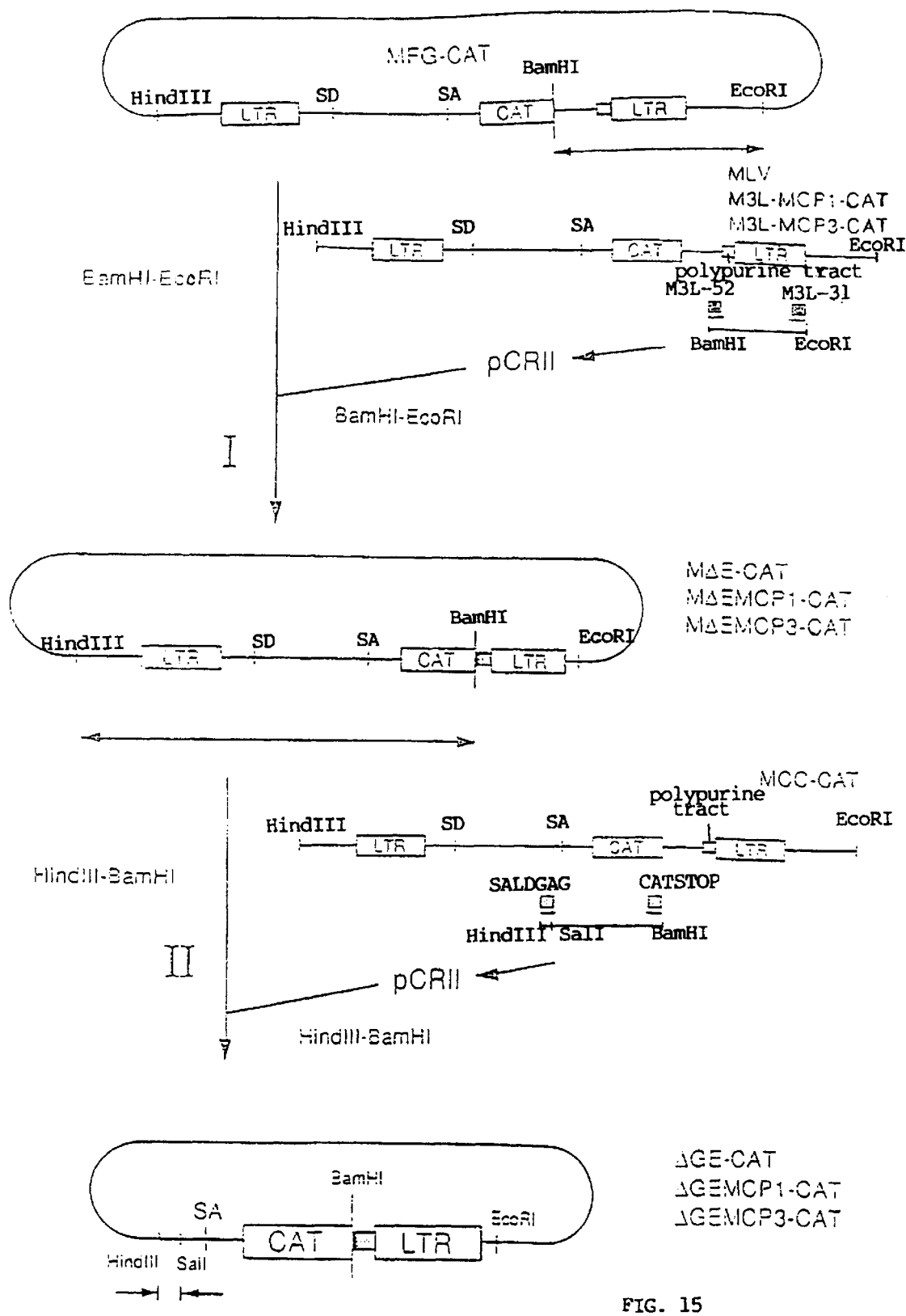
FIG. 15 is a schematic diagram for the construction of CAT-expressing retroviral vectors without gag and env coding sequences, but containing the hybrid U3 and IRES.
Figure 15:
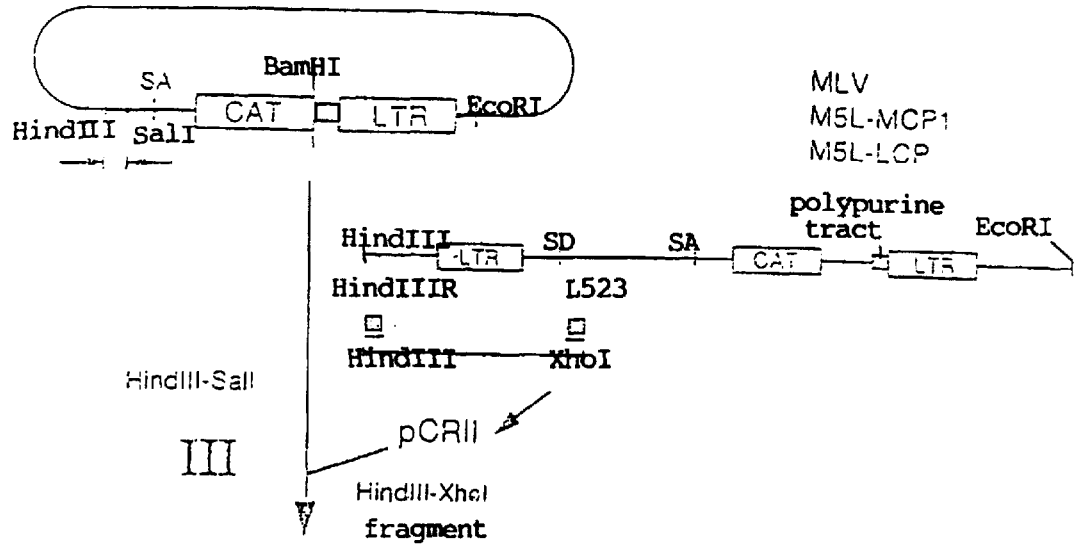
Figure 15:
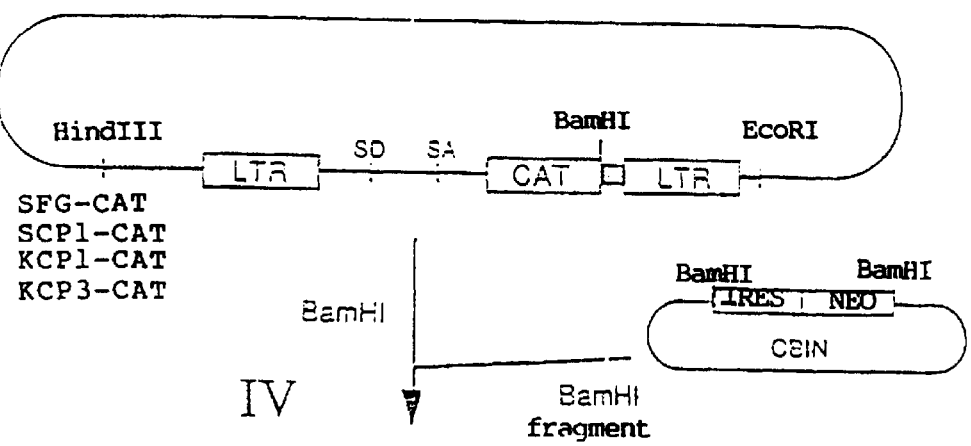
Figure 15:
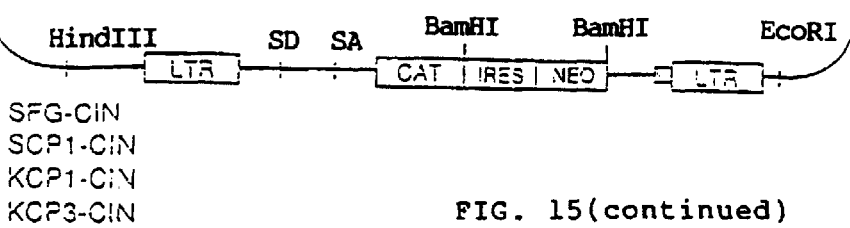

To construct retroviral vectors containing no coding sequences for gag and env, hybrid promoters in both 5'LTR and 3'LTR, CAT and NEO sequences linked by IRES, three plasmids(pMLV, M3LMCP1-CAT, and M3LMCP3-CAT) were amplified with the M3L-52 and M3L-31 primers used for the construction of MΔE-CAT as shown in FIG. 15. The amplified fragments containing BamH I and EcoR I linkers at each end were used to replace the BamH I-EcoR I fragment of MFG-CAT including the 3'LTR, resulting in MΔE-CAT, MΔEMCP1-CAT, and MΔEMCP3-CAT(Step I). The Hind III-BamH I fragments of the latter three plasmids containing the 5'LTR were replaced with the Hind III-BamH I fragment amplified from MCC-CAT(Step II) The nucleotide sequences of primers are as follows:

```
SALDGAG           AAGCTTGTCGACATGAGATCTTATATGGGG
SEQUENCE ID NO:24:HindIII   SalI
```

```
                    -continued
CATSTOP           GGATCCTTACGCCCCGCCCTGCCA
SEQUENCE ID NO:25:BamH I
```

Figure 16:
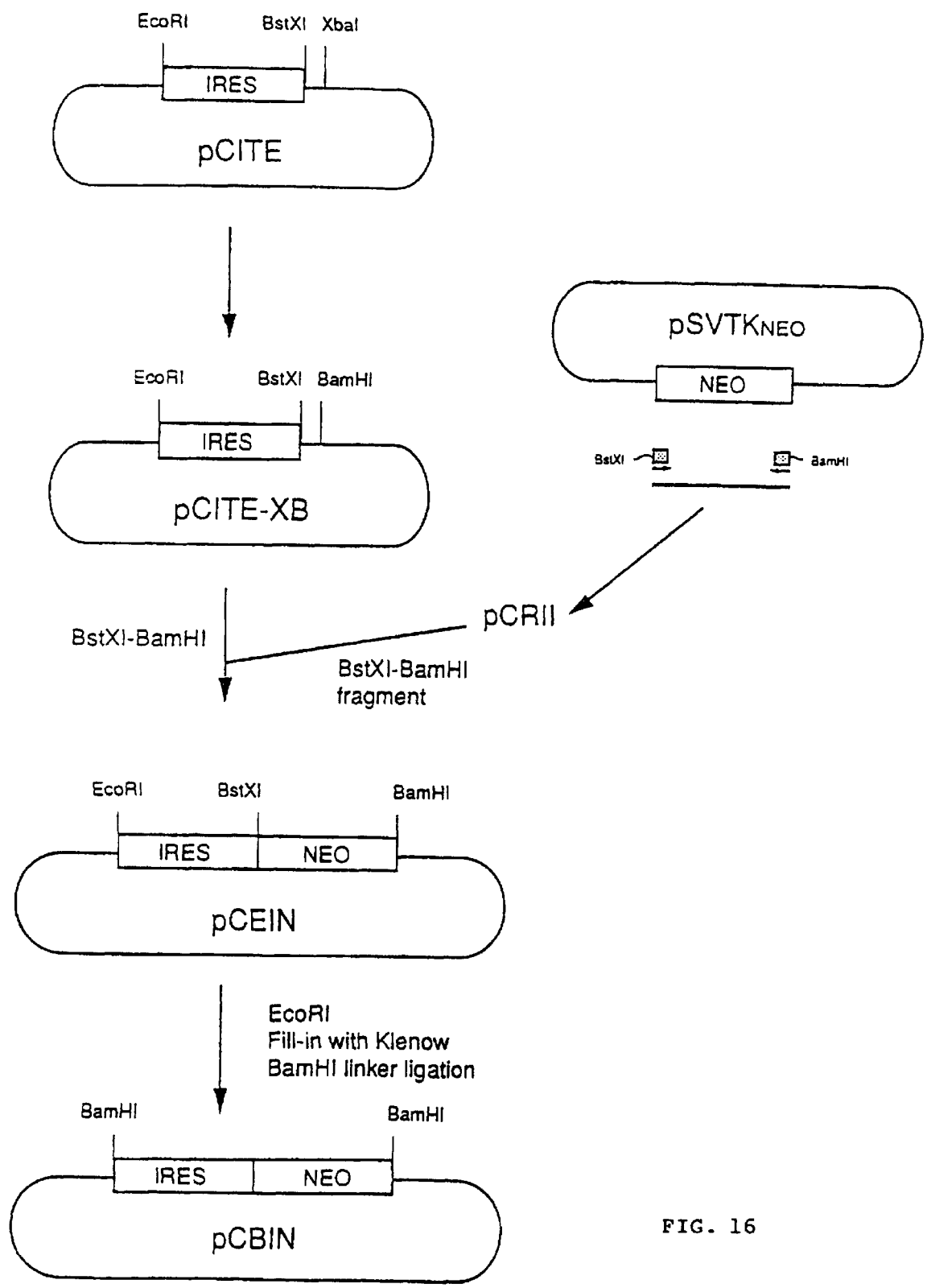
FIG. 16 is a schematic diagram for the construction of the IRES-NEO cassette.

The small Hind III-Sal I fragments of the three intermediate plasmids(ΔGE-CAT, ΔGEMCP1-CAT, and ΔGEMCP3-CAT) were substituted by the Hind III-Xho I fragment amplified from the three plasmids(MLV, M5LMCP1 and M5LCP), resulting in the 4 plasmids SFG-CAT, SCP1-CAT, KCP1-CAT, and KCP3-CAT(Step III). The primers used in this step are HindIIIR and L523. Finally, the BamH I-BamH I cassette containing EMCV IRES/NEO(see: FIG. 16) was inserted into the BamH I site of the 4 plasmids, generating retroviral constructs containing hybrid promoter at both 5' and 3' ends (Step IV). The CAT gene was linked with NEO through EMCV-IRES. The structures of SCP1-CAT and KCP3-CAT constructs are summarized in FIG. 17.

The BamH I-BamH I EMCV IRES-NEO cassette was constructed using pCITE containing EMCV IRES (Novagene, USA), and pSVTK-neo(Stratagene, USA) as shown in FIG. 16. First, the Xba I site of pCITE was converted to BamH I. Secondly, the BstX I-BamH I NEO fragment was prepared by PCR from pSVTKneo. Thirdly, the BstX I-BamH I NEO fragment was inserted to BstX I-BamH I site of pCITE-XB, whose EcoR I was subsequently converted to BamH I, resulting in pCBIN.

Figure 17:
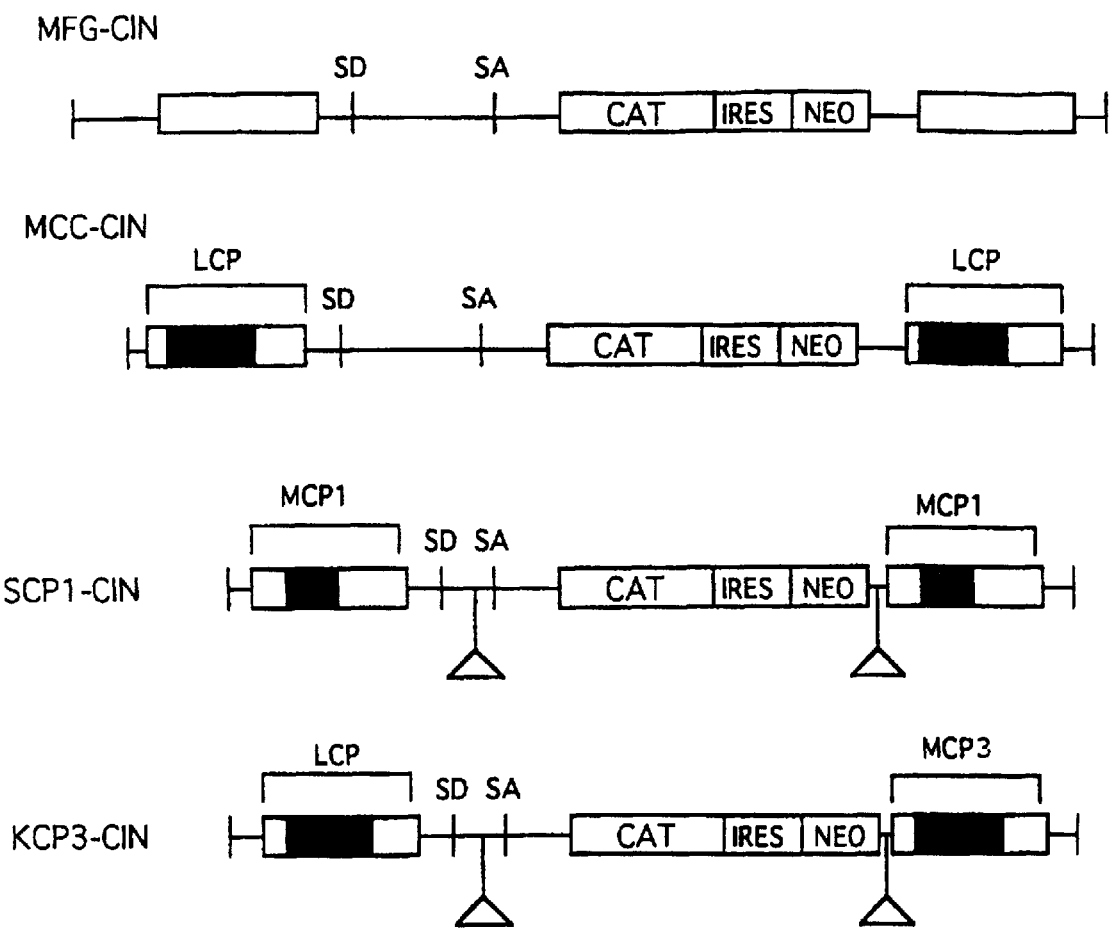
FIG. 17 is a schematic representation of several retroviral vectors containing IRES and NEO, which are prepared by the construction scheme of FIG. 15

In summary, these retroviral vectors were constructed to contain chimeric U3 at both 5' and 3'LTRs, deletions in gag and env coding sequences, and the selectable marker NEO gene linked to CAT through IRES(see: FIG. 17). Retroviral constructs were transfected to CRIP cells, cell-free viral supernatants used to transduce various target cells, and the levels of CAT activity in transduced cells determined. Again, for each cell line, expression of MFG-CIN was set to 1 and those of MCC-CIN, SCP1-CIN, and KCP3-CIN normalized to it. Experimental conditions were identical to others except that one of the target cells was human foreskin fibroblasts (HFF). The result from one representative experiment is shown in Table 2. The novel constructs generally produced levels of CAT activity comparable to the parental construct, suggesting that the two gene could be efficiently expressed in the modified vectors.

TABLE 2

| Cell Line Vector | CEM-SS | HFF | NIH3T3 |
| --- | --- | --- | --- |
| MFG-CIN | 1.0 | 1.0 | 1.0 |
| MCC-CIN | 1.2 | 1.0 | 1.2 |
| SCP1-CIN | 1.0 | 1.7 | 1.2 |
| KCP3-CIN | 1.7 | 2.0 | 1.7 |

*E. coli* HB101 transformed with KCP3-CIN was deposited with an international depository authority(IDA), the Korean Culture Center of Microorganisms (KCCM) on Sep. 19, 1996 as deposition No. KCCM-10110.

Use of a Different Resorter Gene

Figure 18A:
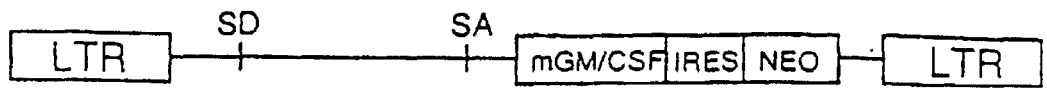
FIG. 18A is a schematic representation of retroviral vectors MFG-mGM/CSF and SCP1-mGM/CSF containing a murine GM-CSF gene as a heterologous gene.
Figure 18A:
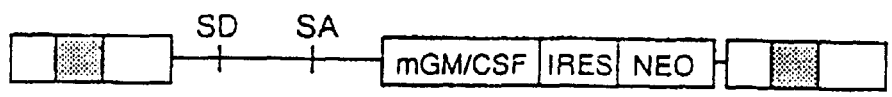
Figure 18B:
FIG. 18B is a histogram showing expression levels of mGM-CSF from CRIP packaging cells transfected with retroviral vectors of FIG. 18A.

The above experiments were performed using the CAT sequence as a reporter gene. To demonstrate that our observation was not restricted to specific reporter gene, the inventors also inserted the murine GM-CSF(mGM-CSF) gene into the SCP1 retroviral vectors SCP1-mGM/CSF was constructed by replacing the Nco I-BamH I CAT sequence in the SCP1-CIN with the Nco I-BamH I mGM/CSF from pCRII-GM/CSF(see: Byun, J. et al., Gene Ther., 3:780–788, 1996; FIG. 18A). The two retroviral vectors expressing mGM-CSF were transfected to CRIP cells(see: FIG. 18B).

Figures 18C, 18D:
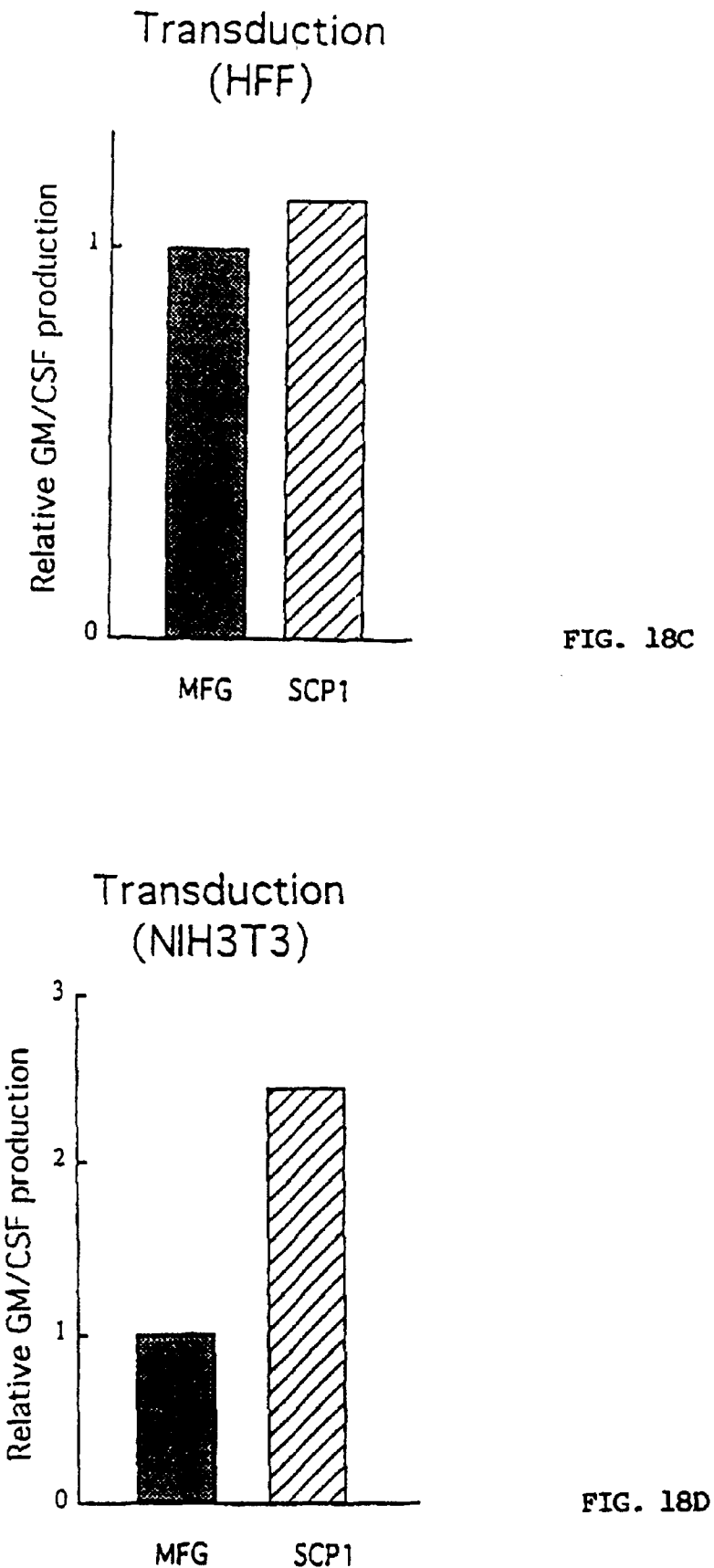
FIG. 18C is a histogram showing expression levels of mGM-CSF from HFF cells transducted with cell-free viral supernatants obtained from the transfected packaging cells of FIG. 18B.
FIG. 18D is a histogram showing expression levels of mGM-CSF from NIH3T3 cells transducted with cell-free viral supernatants obtained from the transfected packaging cells of FIG. 18B.

HFF and NIH3T3 were transduced and then selected in the presence of the antibiotic G418(see: FIGS. 18C and 18D). The same number of drug-resistant cells were plated on 6-cm plates and then grown for another three days. Expression of MFG-mGM/CSF were set to 1. The levels of murine GM-CSF production were determined by enzyme linked immunoadsorbent assay using the commercially available kits from R & D Systems Inc.(Minneapolis, Minn., U.S.A.; MGM00 for mGM-CSF). The newly constructed retroviral vector generally gave slightly higher levels of mGM-CSF in all cell lines tested, confirming the above result based on CAT activity.

EXAMPLE 5

Role of Nco I in Gene Expression

Figure 19A:
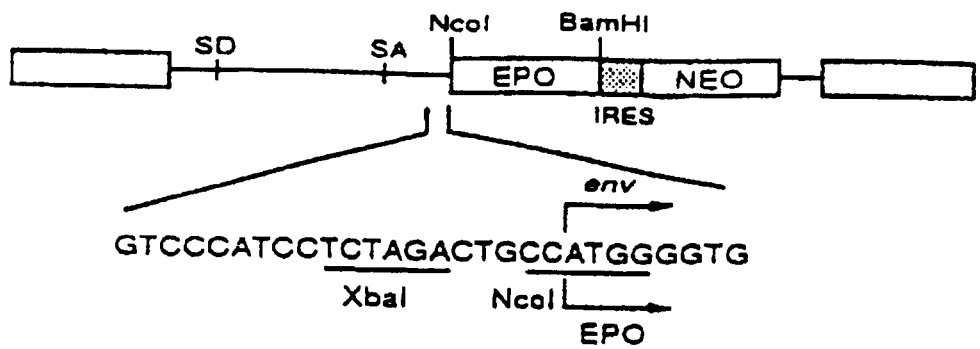
FIG. 19A is a schematic representation of retroviral vectors MFG-WIN, KCP3-WNIN, and KCP3-WXIN.
Figure 19A:
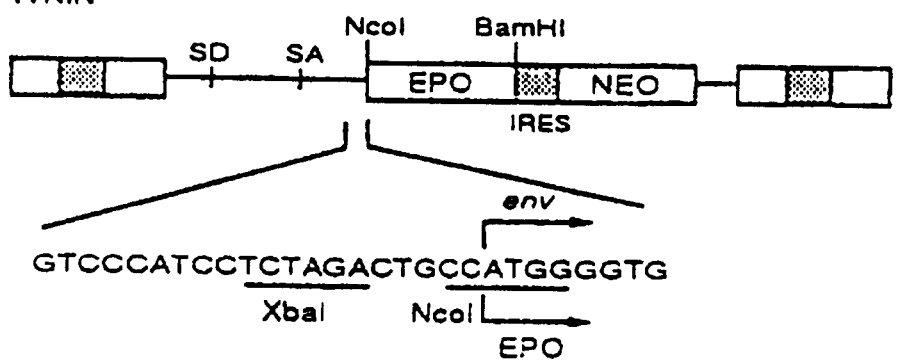
Figure 19A:
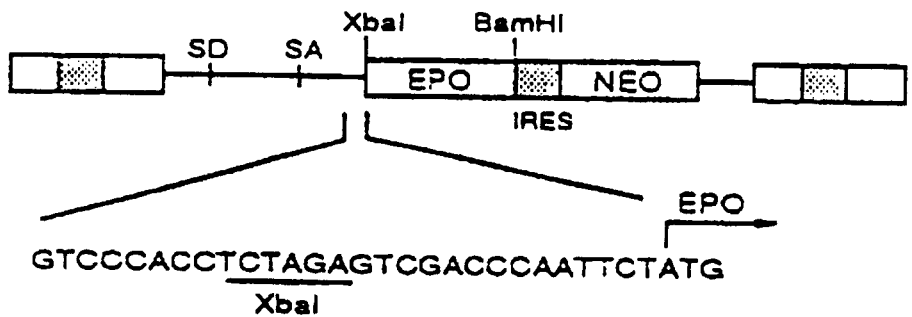

As described, it has been speculated that the use of the Nco I site at the env ATG in MFG is necessary to achieve high levels of protein production. To test whether the initiation codon of a foreign gene has to coincide with the ATG contained within the Nco I cloning site, the two EPO-expressing retroviral vectors KCP3-WNIN and KCP3-WNIN(see: FIG. 19A) that differ in the presence of Nco I site, were compared. KCP3-WNIN was constructed by replacing the Nco I-BamH I CAT sequence with the Nco I-BamH I EPO fragment from pCRII-EPO(see: Byun, J. et al., Gene Ther., 3:780–788, 1996). Next, to construct a retroviral vector lacking a Nco I site, the Nco I site of EPO was filled in by the Klenow fragment and this filled-NcoI/Bam HI EPO gene was then inserted into the filled-XbaI/Bam HI site of KCP3-WNIN, resulting in KCP3-WXIN. The nucleotide sequence environmental around the Nco I site of these vectors and the control vector MFG-WIN is shown in FIG. 19A. In summary, MFG-WIN and KCP3-WNIN contain the NcoI site, while it was removed from KCP3-WXIN.

Figure 19B:
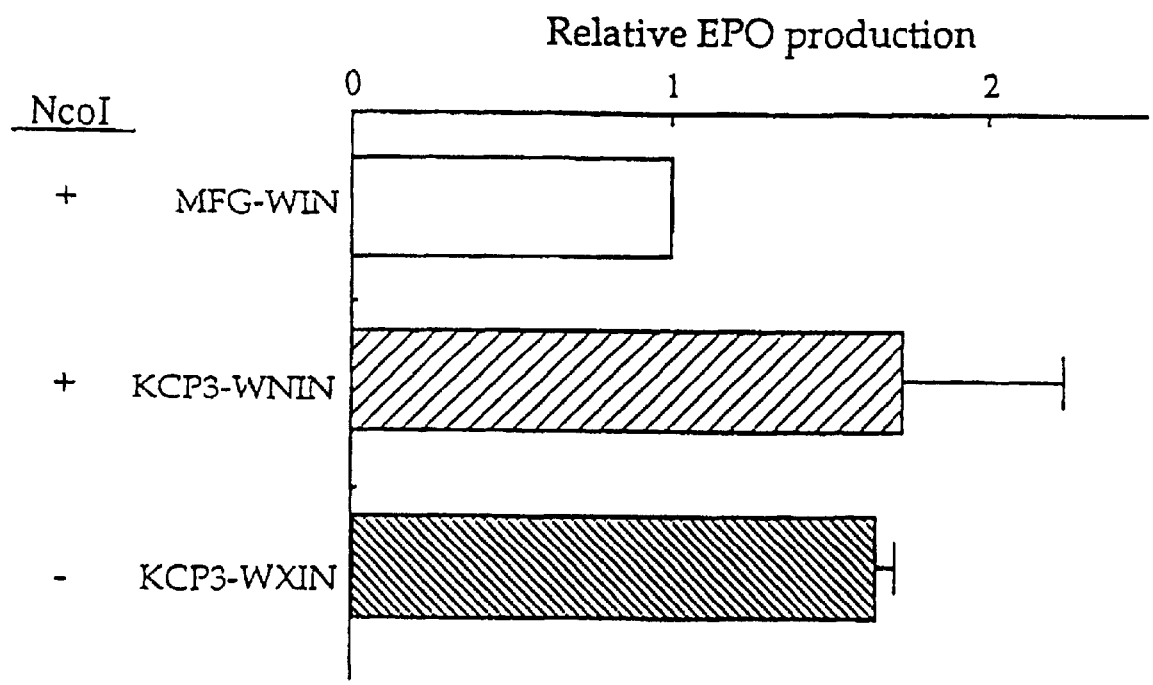
FIG. 19B is a histogram showing effect of gene expression of the retroviral vectors of FIG. 19A.

The three constructs were transfected to CRIP cells, cell-free viral supernatant harvested to transduce NIH3T3 cells followed by G418 selection. The same number of drug-resistant cells were plated on 6-cm plates and then grown for another three days followed by ELISA(see: FIG. 19B). In FIG. 19B, expression of MFG-WIN were set to 1 and those of others normalized to it. The levels of human EPO production were determined by enzyme linked immunoadsorbent assay using the commercially available kits from R & D Systems Inc. (Minneapolis, Minn., U.S.A.; U.S.A. LDEP00 for hEPO). The level of EPO produced from the construct lacking Nco I site was always comparable to the parental vector, indicating that Nco I has marginal, if any, effects on gene expression in the cell lines tested.

EXAMPLE 6

Construction of Retroviral Vectors

Based on the above results, the present inventors constructed a series of retroviral vectors which accommodated the above observations, namely, retroviral vectors in which the gag and env coding sequences unnecessary for packaging were deleted; the U3 sequence not essential for retroviral functions was replaced with heterologous promoter elements; the convenient cloning site was introduced to the truncated U3 so that heterologous full-size promoters or promoter fragments could readily be inserted into U3; IRES was used to express more than one genes; and, the expression site Nco I was replaced with multicloning sites.

The inventors constructed the three sets of retroviral vectors: i.e., (1) vectors containing the chimeric U3 at both 5' and 3'LTR(COI, CTI, COE); (2) vectors containing the original MLV U3(MOI, MTI, MOE); and, (3) vectors containing the convenient cloning site in the truncated U3 (MOMT12, MOMT13).

Figure 20:
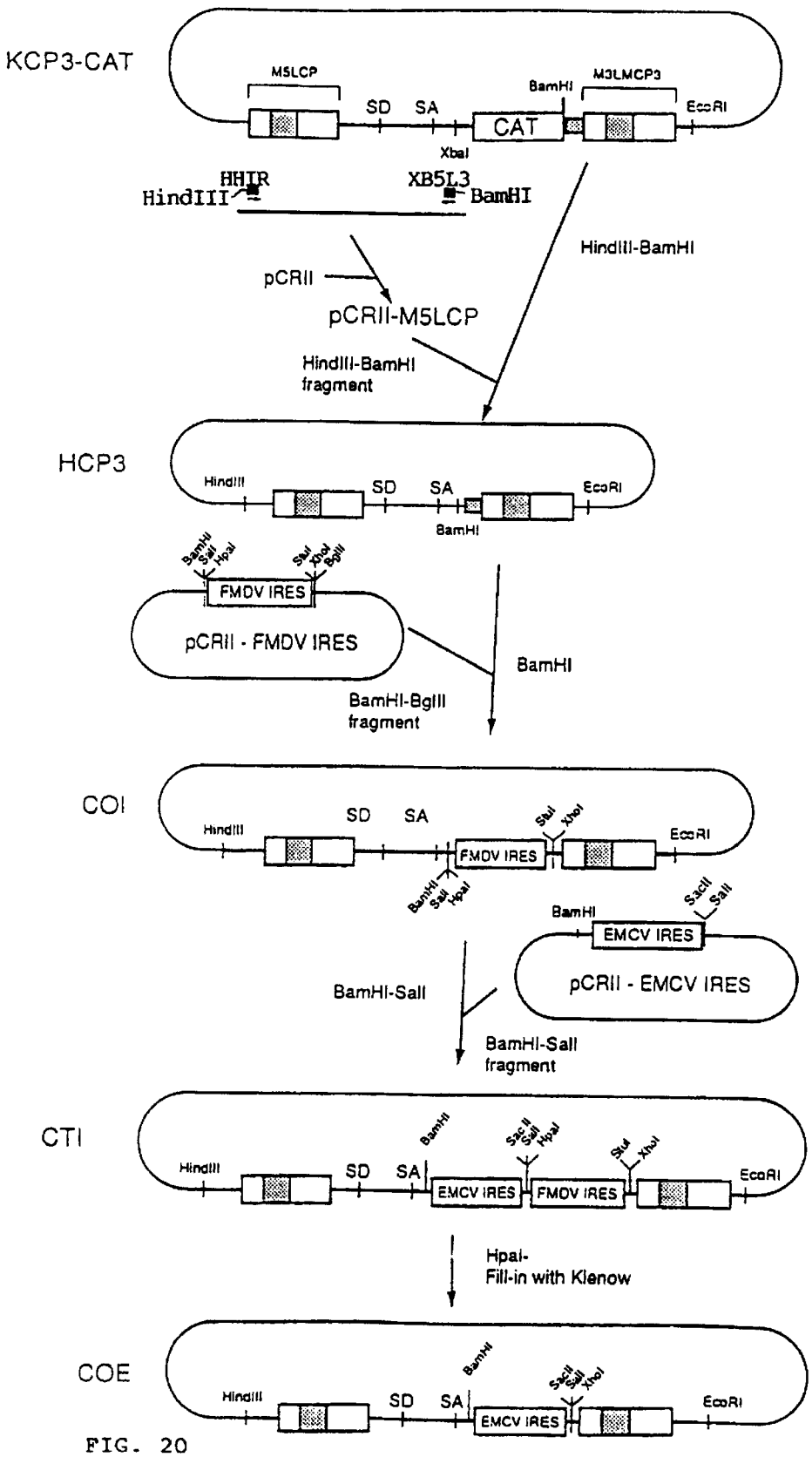
FIG. 20 is a schematic diagram for the construction of improved retroviral vectors COI, CTI, and COE.

To construct the novel, improved retroviral vectors (COI, CTI, COE) in which gene expression is under the control of chimeric U3, the CAT sequence was removed from KCP3-CAT and the Xba I site was converted to BamH I(using pCRII-M5LCP), resulting in HCP3 as shown in FIG. 20. The nucleotide sequence of primers used in this step are HHIR and XB5L3. The former primer was used for construction of RPX68-M5L.

XB5L3 SEQUENCE ID NO:26:  GGATCCTCTAGAGGATGGTC
                          BamHI  XbaI

The BamH I-Bgl II fragment containing PMDV IRES (see: Escarmis, C. et al., Virus Res., 26:113–125, 1992) was inserted into the BamH I site of HCP3, generating COI. Subsequently, the BamH I-Sal I fragment containing EMCV IRES was inserted into the BamH I/Sal I site of COI, resulting in CTI. FMDV IRES was removed from CTI by restriction digestion with Hpa I and Stu I, followed by ligation, generating COE. COI, CTI and COE contain a chimeric U3, identical to that of LCP at the 5'LTR and MCP3 at the 3'LTR. All these vectors have deletions around the gag region(like Δ38 in FIG. 3), no env coding sequence(see: FIG. 6A), the convenient restriction site for the gene of interest, IRES, and NEO as selectable markers.

*E. coli* HB101 transformed with CTI was deposited with an international depository authority(IDA), the Korean Culture Center of Microorganisms(KCCM) on Sep. 8, 1997 as deposition No. KCCM-10109.

Figure 21:
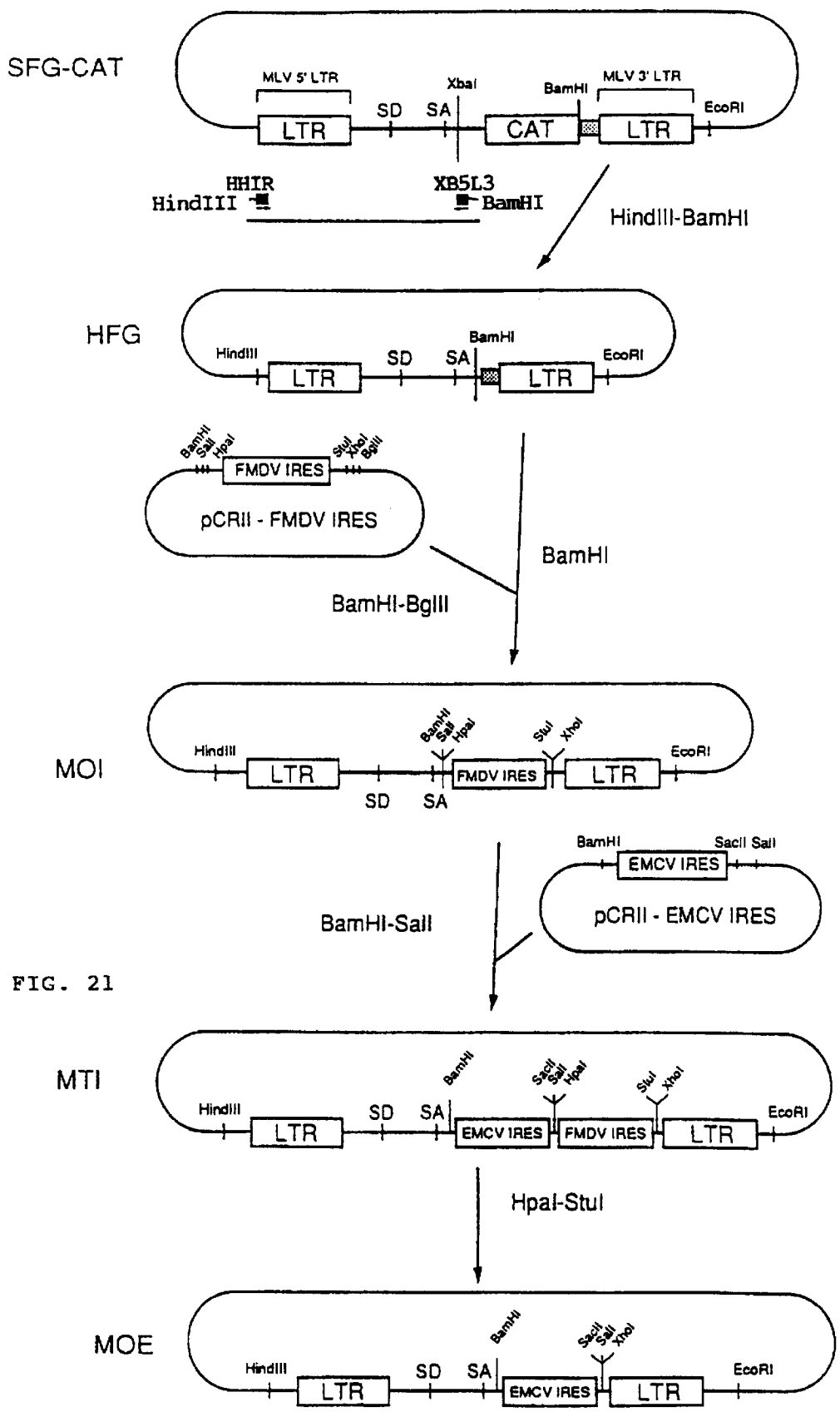
FIG. 21 is a schematic diagram for the construction of improved retroviral vectors MOI, MTI, and MOE.

To construct another set of novel, improved retroviral vectors containing of the original U3 of the MLV LTR (MOI, MTI and MOE), the Xba I-BamH I fragment containing the CAT sequence was first removed from SFG-CAT to generate HFG by amplifying the region between the 5' end of U3 and the naturally occuring Xba I site, just upstream from the start codon of env, using the primers HHIR and XB5L3 (used for construction of HCP3), fusing this Hind III-Xba I fragment with the large Hind III-Xba I fragment of SFG-CAT as shown in FIG. 21. The BamH I-Bgl II fragment containing FMDV-IRES, was then isolated from pCRII-FMDV IRES, and inserted into the BamH I site of HFG, resulting in MOI. Subsequently, the SamH I-Sal I fragment containing EMCV IRES was inserted into the BamH I/Sal I site of MOI, producing MTI. MOE was constructed by cutting MTI with Hpa I and Stu I, and ligating these sites. Therefore, MOE contains only the EMCV IRES.

*E. coli* HB101 transformed with MTI was deposited with an international depository authority(IDA), the Korean Culture Center of Microorganisms(KCCM) on Sep. 8, 1997 as deposition No. KCCM-10108.

The present inventors also constructed the two vectors, MOMT12 and MOMT13, in which heterologous full-size promoters or promoter fragments can be easily inserted into the U3 region. In these vectors, the −419/−152(Nhe I/Xba I) fragment(for MOMT12) and the −419/−1 fragment(for MOMT13) were removed from U3, the restriction linkers inserted to creat a multicloning site, and the truncated U3 placed at the 3'LTR of the vector. Therefore, in these retroviral vectors, heterologous fragments can readily be inserted to the truncated U3 and in transduced cells, the chimeric U3 is translocated to the 5'LTR to drive gene expression.

Figure 22A:
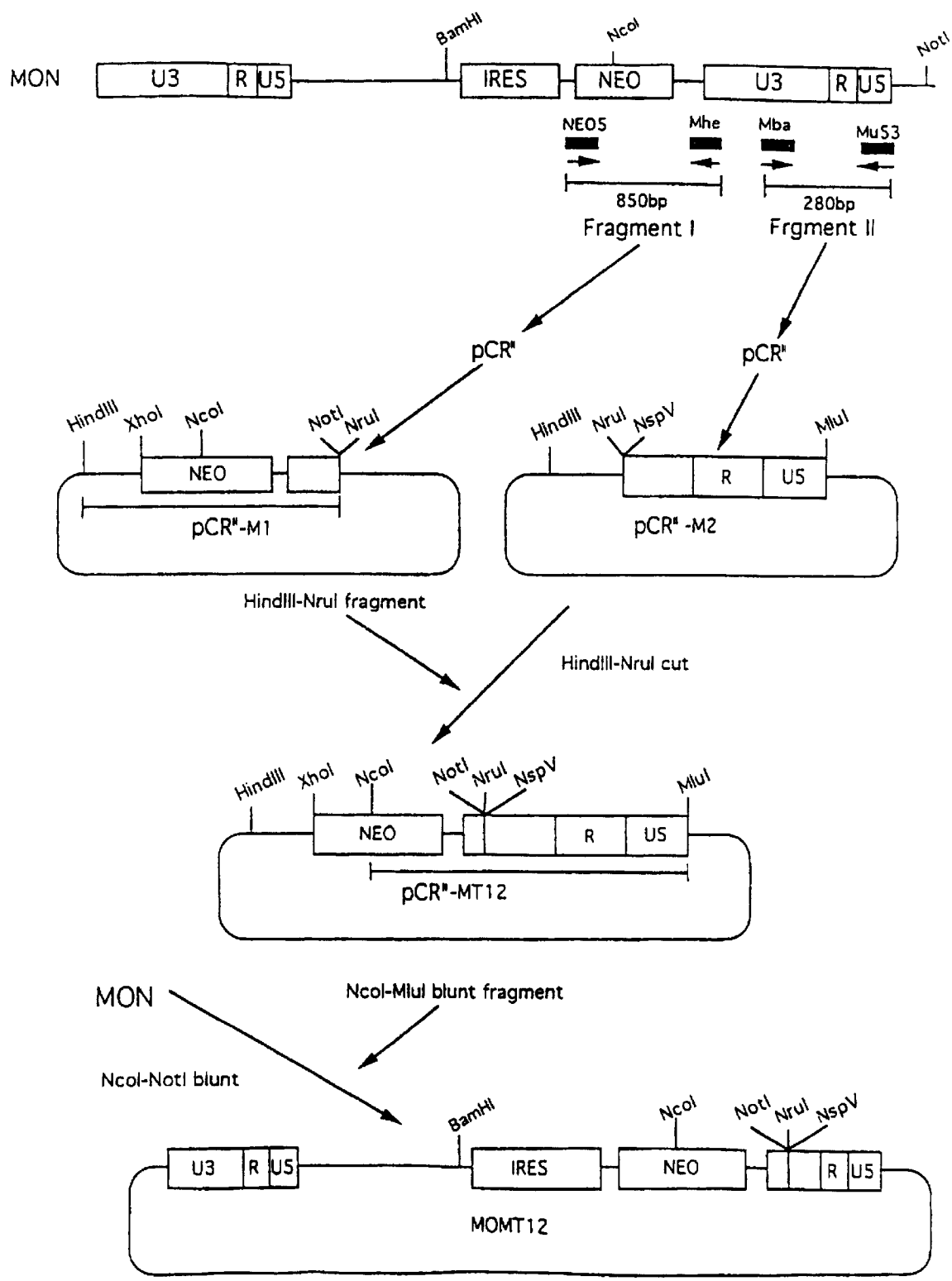
FIG. 22A is a schematic diagram for the construction of improved retroviral vector MOMT12.
Figure 22B:
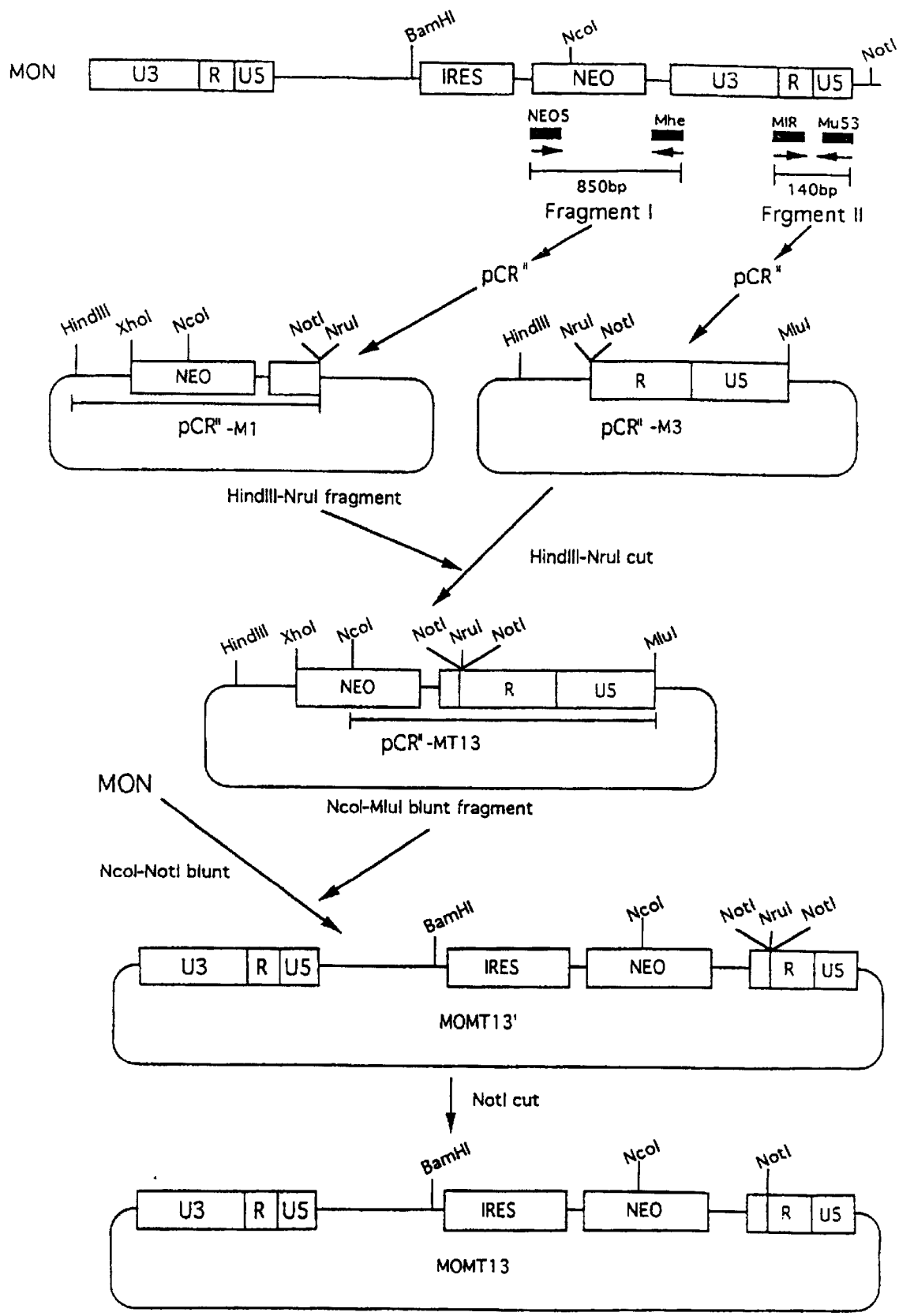
FIG. 22B is a schematic diagram for the construction of retroviral vector MOMT13.
Figure 22C:
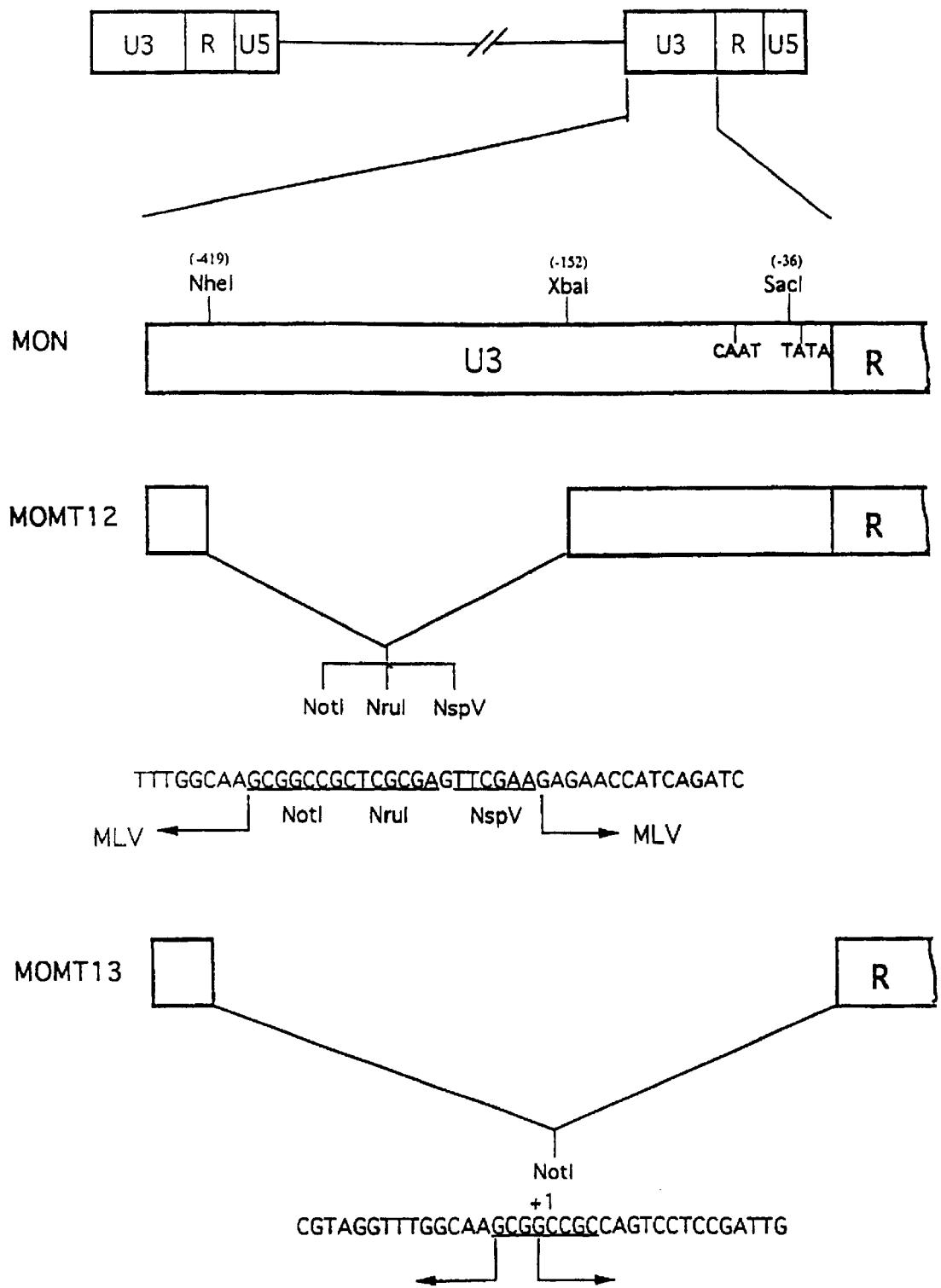
FIG. 22C is a schematic representation of retroviral vectors MOMT12 and MOMT13.

MOMT12 was constructed as illustrated in FIG. 22A. First, the two fragments were amplified from MON which is MOI containing NEO at its Xho I site by PCR using the two pairs of primers as shown in FIG. 22A and cloned into pCRII, resulting in pCRII-M1 and pCRII-M2. The two plasmids were cut with Hind III and Nru I and the appropriate fragments ligated with each other as indicated in FIG. 22A, generating pCRII-MT12. pCRII-MT12 were digested with Nco I and Mlu I, and blunt-ended. MON was digested with Nco I and Not I, blunt-ended, and ligated with blunt-ended pCRII-MT12, resulting in MOMT12. MOMT13 was constructed in the same way except that pCRII-M3 was made from MON instead of PCRII-M2(see: FIG. 22B). The precise deletion end points of U3 are as indicated in FIG. 22C.

The nucleotide sequences of primers used for construction of these two plasmid are:

```
NEO5 SEQUENCE ID NO:27:   CTCGAGATGGGATCGGCC
                          Xha I

Mhe  SEQUENCE ID NO:28:   TCGCGAGCGGCCGCTTGCCAAACCTACAGGTGG
                          Nru I  Not I

Mba  SEQUENCE ID NO:29:   TCGCGAGTTCGAAGAGAACCATCAGATG
                          Nru I   Nsp V

Mu53 SEQUENCE ID NO:30:   ACGCGTATCGATGAAAGACCCCCGCTGACG
                          Mlu I   Cla I

MIR  SEQUENCE ID NO:31:   TCGCGAGCGGCCGCCAGTCCTCCGATTG
                          Nru I    Not I
```

Test for Levels of Gene Expression and Viral Titers

To confirm that these newly constructed vectors function as expected, the inventors took the two retroviral vectors, MOI and COI, and tested them for their levels of gene expression and viral titers.

Figure 23A:
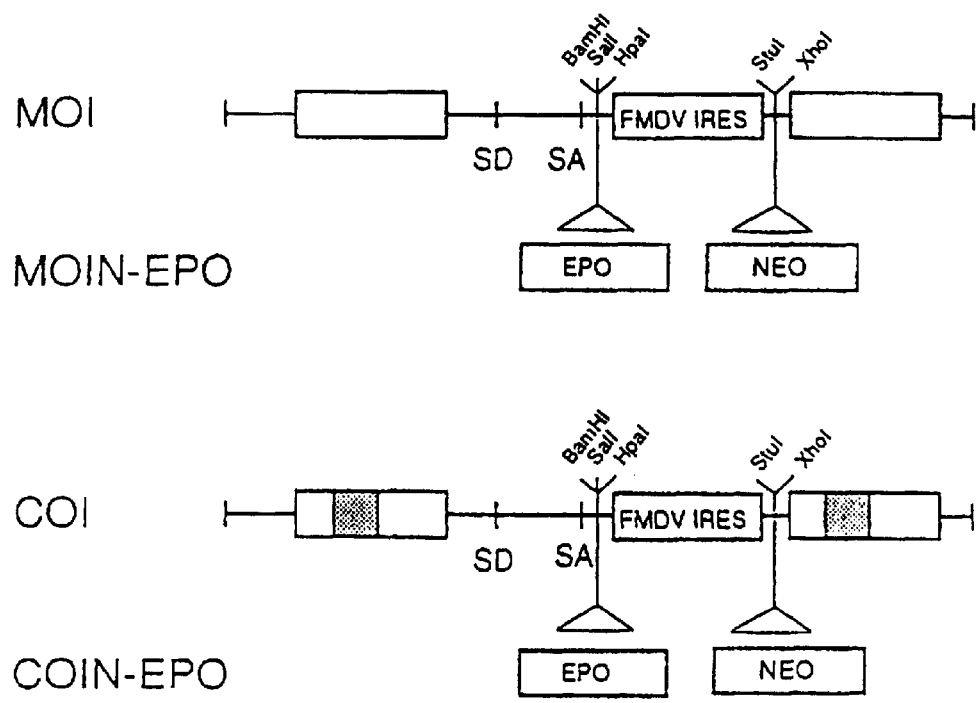
FIG. 23A is a schematic representation of retroviral vectors MOI, MOIN-EPO, COI, and COIN-EPO.

The NEO sequence was added to the Xho I site of MOI and COI, resulting in MOIN and COIN respectively. The EPO cDNA sequence was subsequently cloned into the BamH I site of MOIN and COIN, generating MOIN-EPO and COIN-EPO(see: FIG. 23A). E. coli HB101 transformed with COIN-EPO was deposited with an international depository authority(IDA), the Korean Culture Center of Microorganisms(KCCM) on May 15, 1997 as deposition No. KCCM-10099.

MOIN-EPO and COIN-EPO, together with the parental construct MFG-WIN, were transfected into CRIP or SING cells, and cell-free viral supernatants were harvested to transduce NIH3T3 cells. Viral titer were determined 3 days post-transduction. Cells were selected in the presence of the anibiotic G418 to be close to the actual situation.

Figure 23B:
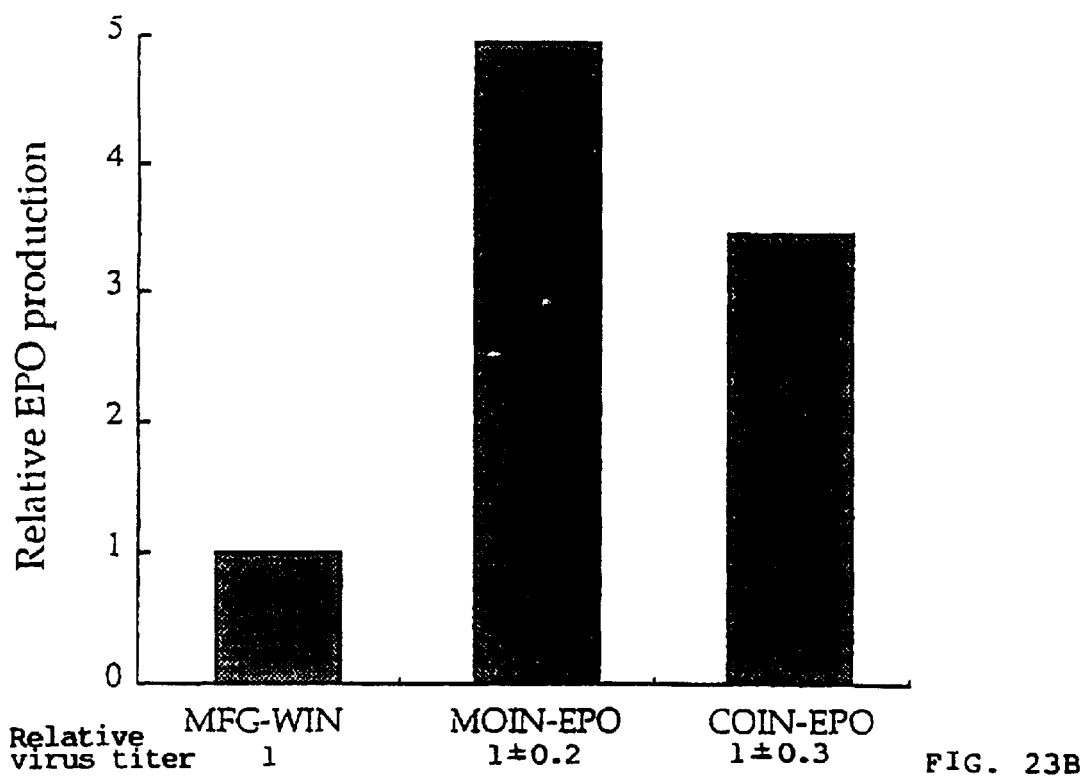
FIG. 23B is a histogram showing effect of gene expression of the retroviral vectors MFG-WIN, MOIN-EPO, and COIN-EPO, together with relative virus titers shown at the bottom of the histogram.

Drug-resistant populations were obtained. Identical numbers of cells were plated on 6-cm culture plate and the levels of EPO in the culture supernatant compared after 3 days. The improved vector always gave higher levels of EPO, while viral titers were comparable between these novel vectors and the parental MFG-based construct(see: FIG. 23B).

In addition, to confirm that these newly constructed vectors lacking the entire gag coding sequence could indeed produce viral titers comparable to MFG, the inventors transfected the amphotropic packaging line PA317 with MFG-, MOI-, and COI-based retroviral vectors expressing EPO. G418-resistant PA317 populations were generated and compared for viral titers at similar cell concentrations as previously described(see: Byun et al., Gene Ther., 3:1018–1020, 1996). As indicated in FIG. 23B, viral titers were always comparable between the three vectors, confirming the previous finding that the deletion of the gag coding sequence indeed has no significant effect on viral packaging.

Preservation of Retroviral Sequences in Transduced Target Cells

Figure 24:
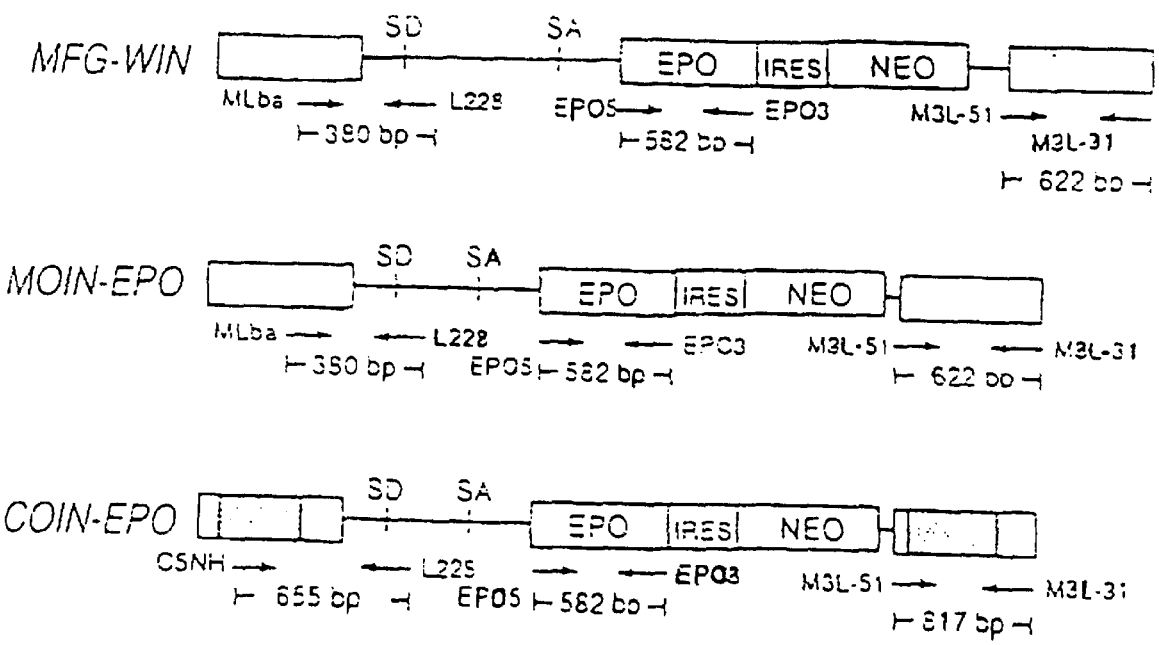
FIG. 24 is a schematic representation of 5'LTR, EPO and 3'LTR positions to be amplified by PCR on retroviral vectors MFG-WIN, MOIN-EPO, and COIN-EPO.

The present inventors have also demonstrated, using PCR, that the nucleotide sequence in the retroviral vectors was preserved in the transduced target cells. For this, total DNA was prepared by lysing transduced- and selected-NIH3T3 cell line using TES(10 mM Tris-HCl(pH 7.8), 1 mM EDTA, 0.7% SDS) followed by the treatment with 400 μg/ml proteinase K at 50° C. for 1 hour, phenol:chloroform extraction, and ethanol precipitation. The polymerase chain reaction(PCR) was performed using 5 μg of total genomic DNA and the following oligonucleotide primers specific to various region of the retroviral vector as indicated in FIG. 24.

```
MLba              TCGCGAGTCGAAGAGAACCATCAGATG
SEQUENCE ID NO:32:

L228              GCCTCGAGATAAGTTGCTGGCCAG
SEQUENCE ID NO:33:

C5NH              GCTAGCGGGACTTTCCATTGACGT
SEQUENCE ID NO:34:

EPC5              CCATGGGGCTGCAGAAT
SEQUENCE ID NO:35:

EPC3              GGATCCTCATTTTTGGACTGG
SEQUENCE ID NO:36:
```

The samples were amplified through 30 cycles that included the following parameters; denaturation at 94° for 1 min, primer annealing at 55° C. for 1 min, and primer extension at 72° C. for 1 min and 30 sec. The amplified DNA fragments were analysed by agarose gel eletrophoresis.

If the retroviral vectors stably transfer the retroviral sequences to the target cells, these primers would amplify 380,582, and 622 bp of the 5' region of the viral genome, EPO, and the 3'LTR from MFG-WIN or MOIN-EPO respectively, while 655, 582, and 617 bp from COIN-EPO. DNA fragments of expected lengths were present in all cells, suggesting that the novel vectors can stably transfer the foreign gene to target cells.

Tests for Replication-competent Virus

The producer lines containing MFG-, MOI- and COI-based retroviral vectors were shown to be free of RCR by a BAG mobilization assay and RT-PCR of the retroviral env gene.

The BAG mobilization assay was carried out as described by Pear et al's publication(see: Pear et al., Proc. Natl. Acad. Sci., USA, 90:8392–8396, 1993). Three milliliter of supernatant from producer lines was used to infect BAG cells(see: Price et al., Proc. Natl. Acad. Sci., USA, 84:156–160, 1987), and the cells were passaged 1:10 every 3 or 4 days. When passage 3 of the infected BAG cells had reached approximately 50% confluence, the medium was changed, and 24 hours later, the supernatant was filtered with 0.45 μm pore membrane. Three milliliter of the filtrate was used to infect NIH3T3 cells and 48 hours later, the cells were divided into two; one was stained for β-gal, while the other underwent G418 selection. To determine the titer of the virus used to infect BAG cells, 1 ml of the viral supernatant from the virus-producer cells was used in parallel to infect NIH3T3 followed by G418 selection.

No X-gal stained or G418-resistant cells were found from any producer lines tested in this experiment, suggesting that at a given sensitivity of the assay, no RCR was produced from the newly constructed vectors.

Amphotropic retroviral env gene was also amplified by PCR from recombinant viral and transduced cellular genome. Virus-producing cells were seeded at 5×10⁶ per 100 mm-diameter dish, and virus-containing medium was harvested 48 hours later. Recombinant virus were harvested by ultracentrifugation at 35,000 g for 2 hours in an SW50.1 after 0.45 μm-pore syringe filtration. Viral pellet were resuspended in 200 ml of TES, and 100 μg of proteinase K was added to samples and incubated 30 minutes at 37° C. After a phenol-chloroform extraction, 5 U of RNase free-DNase (Promega, U.S.A.) was added to samples and incubated 37° C. for 30 minutes. After one more phenol-chloroform extraction, RNAs were precipitated with ethanol and pellets were resuspended with 50 ml of DEPC (diethylpyrocarbonate) water. Viral cDNAs were sythesized from the viral RNAs by AMV-RT(Promega, USA). Reverse transcription was initiated from MLV 3'LTR-specific oligomer, MLhe and incubated with dNTPs and RNase inhibitor at 42° C. for 1 hour.

MLhe              TCGCGAGCGGCCGCTGCCAAACCTACG
SEQUENCE ID NO:37:

Synthesized cDNAs were used as a template of PCR. The env gene of recombinant viral and transduced cellular genome were amplified using MLV-E5 and MLV-E3 primers as follows:

MLV-E5            AAGCTTATGGCGCGTTCAACGCTCTCA
SEQUENCE ID NO:38:

MLV-E3            AAGCTTCTATGGCTCGTACTCTATAGG
SEQUENCE ID NO:39:

This result was also confirmed by RT-PCR of culture supernatants from the producer lines using the oligonucleotide primers that can amplify the retroviral env gene.

As clearly illustrated and demonstrated as aboves, the present invention provides retroviral vectors lacking coding sequences for gag and env which are not essential for viral functions. The vectors are safe, as the possibility of homologous recombination between the packaging genome and the vector is minimized, which in turn reduces the possibility of generation of replication-competent retrovirus(RCR), and they allow easy insertion of a large foreign DNA fragment. The retroviral vectors were also designed so that the almost entire U3 can readily be substituted with full-size heterologous promoters or their fragments containing nucleotide sequences completely different from the original U3, whereby the vectors can readily be converted to have their gene expression regulated in a various and sophisticated manner. Furthermore, the vectors allow the insertion of internal ribosomal entry sites(IRES) and multicloning sites, which renders them simultaneous expression of 2 or 3 genes of interest.

What is claimed is:

1. A murine leukemia virus (MLV) based retroviral for delivering a gene of interest to a target cell, wherein the entire Gag, and Env, coding sequences are deleted and th comprises one or two internal ribosomal entry sites.

2. The retroviral vector of claim 1, wherein the gene of interest is located downstream from both a splice donor site and a splice acceptor site.

3. The retroviral vector of claim 1, wherein the gene of interest is selected from the group consisting of genes which produces a hormone, an enzyme, a receptor and a drug of interest.

4. The retroviral vector of claim 1, wherein all or part of at least one U3 sequence of a 5'LTR and a 3'LTR obtained from a retrovirus is substituted with a major immediate-early promoter of human cytomegalovirus which is selected from the group consisting of CR, CCI, CCII and CP.

5. The retroviral vector of claim 4, which further comprises a multicloning site at the truncated U3 of the 3'LTR, to facilitate the insertion of the major immediate-early promoter of human cytomegalovirus or the fragment thereof which is selected from the group consisting of CR, CCI, CCII and CP thereto.

6. The retroviral vector of claim 4, wherein the major immediate-early promoter of human cytomegalovirus is regulated at the transcription level by the aid of a chemical or a biological molecule.

7. The retroviral vector of claim 6, wherein the biological molecule is selected from the group consisting of hormone, growth factor, enzyme, lymphokine and cytokine.

8. The retroviral vector of claim 1, wherein the internal ribosomal entry sites are obtained from murine encephalomyocarditis virus (EMCV) or foot and mouth disease virus (FMDV).

9. The retroviral vector of claim 1, wherein each of the two internal ribosomal entry sites are obtained from viral sources different from each other.

10. The retroviral vector of claim 1, which further comprises a multicloning site downstream from the splice acceptor site or upstream from the internal ribosomal entry sites, to facilitate the insertion of a gene of interest.

* * * * *

SEQUENCE LISTING

<160> NUMBER OF SEQ ID NOS: 39

<210> SEQ ID NO 1
<211> LENGTH: 17
<212> TYPE: DNA
<213> ORGANISM: Artificial Sequence
<220> FEATURE:
<223> OTHER INFORMATION: HindIIIR, single-stranded oligonucleotide

<400> SEQUENCE: 1
gcattaaagc tttgctc                                                        17

<210> SEQ ID NO 2
<211> LENGTH: 24
<212> TYPE: DNA
<213> ORGANISM: Artificial Sequence
<220> FEATURE:
<223> OTHER INFORMATION: L228, single-stranded oligonucleotide

<400> SEQUENCE: 2
gcctcgagat aagttgctgg ccag                                              24

<210> SEQ ID NO 3
<211> LENGTH: 24
<212> TYPE: DNA
<213> ORGANISM: Artificial Sequence

```
<220> FEATURE:
<223> OTHER INFORMATION: L377, single-stranded oligonucleotide

<400> SEQUENCE: 3
gcctcgagtc cctgggacgt ctcc                                              24

<210> SEQ ID NO 4
<211> LENGTH: 24
<212> TYPE: DNA
<213> ORGANISM: Artificial Sequence
<220> FEATURE:
<223> OTHER INFORMATION: L523, single-stranded oligonucleotide

<400> SEQUENCE: 4
gcctcgagca aaaattcaga cgga                                              24

<210> SEQ ID NO 5
<211> LENGTH: 23
<212> TYPE: DNA
<213> ORGANISM: Artificial Sequence
<220> FEATURE:
<223> OTHER INFORMATION: L739, single-stranded oligonucleotide

<400> SEQUENCE: 5
gcctcgagca gaaggtaacc caa                                               23

<210> SEQ ID NO 6
<211> LENGTH: 25
<212> TYPE: DNA
<213> ORGANISM: Artificial Sequence
<220> FEATURE:
<223> OTHER INFORMATION: R371, single-stranded oligonucleotide

<400> SEQUENCE: 6
gcctcgaggg acttcggggg gccgt                                             25

<210> SEQ ID NO 7
<211> LENGTH: 24
<212> TYPE: DNA
<213> ORGANISM: Artificial Sequence
<220> FEATURE:
<223> OTHER INFORMATION: R527, single-stranded oligonucleotide

<400> SEQUENCE: 7
gcctcgaggt ttgggaccga agcc                                              24

<210> SEQ ID NO 8
<211> LENGTH: 24
<212> TYPE: DNA
<213> ORGANISM: Artificial Sequence
<220> FEATURE:
<223> OTHER INFORMATION: R743, single-stranded oligonucleotide

<400> SEQUENCE: 8
gcctcgagaa tggccaacct ttaa                                              24

<210> SEQ ID NO 9
<211> LENGTH: 24
<212> TYPE: DNA
<213> ORGANISM: Artificial Sequence
<220> FEATURE:
<223> OTHER INFORMATION: R1016, single-stranded oligonucleotide

<400> SEQUENCE: 9
gcctcgagcc ctcactcctt ctct                                              24
```

```
<210> SEQ ID NO 10
<211> LENGTH: 18
<212> TYPE: DNA
<213> ORGANISM: Artificial Sequence
<220> FEATURE:
<223> OTHER INFORMATION: ClaIL, single-stranded oligonucleotide

<400> SEQUENCE: 10
acgctcatcg ataatttc                                                    18

<210> SEQ ID NO 11
<211> LENGTH: 18
<212> TYPE: DNA
<213> ORGANISM: Artificial Sequence
<220> FEATURE:
<223> OTHER INFORMATION: M3L-52, single-stranded oligonucleotide

<400> SEQUENCE: 11
aaaggatcca tttagtct                                                    18

<210> SEQ ID NO 12
<211> LENGTH: 26
<212> TYPE: DNA
<213> ORGANISM: Artificial Sequence
<220> FEATURE:
<223> OTHER INFORMATION: M3L-31, single-stranded oligonucleotide

<400> SEQUENCE: 12
gaattcatgt gaaaggcggc cgctga                                           26

<210> SEQ ID NO 13
<211> LENGTH: 24
<212> TYPE: DNA
<213> ORGANISM: Artificial Sequence
<220> FEATURE:
<223> OTHER INFORMATION: C5NH, single-stranded oligonucleotide

<400> SEQUENCE: 13
gctagcggga ctttccattg acgt                                             24

<210> SEQ ID NO 14
<211> LENGTH: 34
<212> TYPE: DNA
<213> ORGANISM: Artificial Sequence
<220> FEATURE:
<223> OTHER INFORMATION: C3KP, single-stranded oligonucleotide

<400> SEQUENCE: 14
gggtacccgg gcgactcagt caatcggagg agga                                  34

<210> SEQ ID NO 15
<211> LENGTH: 20
<212> TYPE: DNA
<213> ORGANISM: Artificial Sequence
<220> FEATURE:
<223> OTHER INFORMATION: CCI-5, single-stranded oligonucleotide

<400> SEQUENCE: 15
cgatcgccgc gttacataac                                                  20

<210> SEQ ID NO 16
<211> LENGTH: 21
<212> TYPE: DNA
<213> ORGANISM: Artificial Sequence
<220> FEATURE:
<223> OTHER INFORMATION: CCI-3, single-stranded oligonucleotide
```

<400> SEQUENCE: 16
tctagaggaa actcccgtaa g                    21

<210> SEQ ID NO 17
<211> LENGTH: 20
<212> TYPE: DNA
<213> ORGANISM: Artificial Sequence
<220> FEATURE:
<223> OTHER INFORMATION: CCII-5, single-stranded oligonucleotide

<400> SEQUENCE: 17
tctagaggtt tgactcacgg                      20

<210> SEQ ID NO 18
<211> LENGTH: 20
<212> TYPE: DNA
<213> ORGANISM: Artificial Sequence
<220> FEATURE:
<223> OTHER INFORMATION: CCII-3, single-stranded oligonucleotide

<400> SEQUENCE: 18
gagctcccta ccgcccecattt                    20

<210> SEQ ID NO 19
<211> LENGTH: 25
<212> TYPE: DNA
<213> ORGANISM: Artificial Sequence
<220> FEATURE:
<223> OTHER INFORMATION: HHIR, single-stranded oligonucleotide

<400> SEQUENCE: 19
aagcttatgt gaaagacccc tcctg                25

<210> SEQ ID NO 20
<211> LENGTH: 21
<212> TYPE: DNA
<213> ORGANISM: Artificial Sequence
<220> FEATURE:
<223> OTHER INFORMATION: 5LBG, single-stranded oligonucleotide

<400> SEQUENCE: 20
agatctggcg cctagagaag g                    21

<210> SEQ ID NO 21
<211> LENGTH: 24
<212> TYPE: DNA
<213> ORGANISM: Artificial Sequence
<220> FEATURE:
<223> OTHER INFORMATION: M3L-51, single-stranded oligonucleotide

<400> SEQUENCE: 21
aaaggatccg attagtccaa tttg                 24

<210> SEQ ID NO 22
<211> LENGTH: 22
<212> TYPE: DNA
<213> ORGANISM: Artificial Sequence
<220> FEATURE:
<223> OTHER INFORMATION: BGSA, single-stranded oligonucleotide

<400> SEQUENCE: 22
atgagatctt atatggggca cc                   22

<210> SEQ ID NO 23

<210> SEQ ID NO 23
<211> LENGTH: 40
<212> TYPE: DNA
<213> ORGANISM: Artificial Sequence
<220> FEATURE:
<223> OTHER INFORMATION: NcoE3, single-stranded oligonucleotide

<400> SEQUENCE: 23
ggatccggcc atggctgtct agaggatggt cctcccccgg                40

<210> SEQ ID NO 24
<211> LENGTH: 30
<212> TYPE: DNA
<213> ORGANISM: Artificial Sequence
<220> FEATURE:
<223> OTHER INFORMATION: SALDGAG, single-stranded oligonucleotide

<400> SEQUENCE: 24
aagcttgtcg acatgagatc ttatatgggg                30

<210> SEQ ID NO 25
<211> LENGTH: 24
<212> TYPE: DNA
<213> ORGANISM: Artificial Sequence
<220> FEATURE:
<223> OTHER INFORMATION: CATSTOP, single-stranded oligonucleotide

<400> SEQUENCE: 25
ggatccttac gccccgccct gcca                24

<210> SEQ ID NO 26
<211> LENGTH: 20
<212> TYPE: DNA
<213> ORGANISM: Artificial Sequence
<220> FEATURE:
<223> OTHER INFORMATION: XB5L3, single-stranded oligonucleotide

<400> SEQUENCE: 26
ggatcctcta gaggatggtc                20

<210> SEQ ID NO 27
<211> LENGTH: 18
<212> TYPE: DNA
<213> ORGANISM: Artificial Sequence
<220> FEATURE:
<223> OTHER INFORMATION: NEO5, single-stranded oligonucleotide

<400> SEQUENCE: 27
ctcgagatgg gatcggcc                18

<210> SEQ ID NO 28
<211> LENGTH: 33
<212> TYPE: DNA
<213> ORGANISM: Artificial Sequence
<220> FEATURE:
<223> OTHER INFORMATION: Mhe, single-stranded oligonucleotide

<400> SEQUENCE: 28
tcgcgagcgg ccgcttgcca aacctacagg tgg                33

<210> SEQ ID NO 29
<211> LENGTH: 28
<212> TYPE: DNA
<213> ORGANISM: Artificial Sequence
<220> FEATURE:
<223> OTHER INFORMATION: Mba, single-stranded oligonucleotide

<400> SEQUENCE: 29
tcgcgagttc gaagagaacc atcagatg                                        28

<210> SEQ ID NO 30
<211> LENGTH: 30
<212> TYPE: DNA
<213> ORGANISM: Artificial Sequence
<220> FEATURE:
<223> OTHER INFORMATION: Mu53, single-stranded oligonucleotide

<400> SEQUENCE: 30
acgcgtatcg atgaaagacc cccgctgacg                                      30

<210> SEQ ID NO 31
<211> LENGTH: 28
<212> TYPE: DNA
<213> ORGANISM: Artificial Sequence
<220> FEATURE:
<223> OTHER INFORMATION: MIR, single-stranded oligonucleotide

<400> SEQUENCE: 31
tcgcgagcgg ccgccagtcc tccgattg                                        28

<210> SEQ ID NO 32
<211> LENGTH: 28
<212> TYPE: DNA
<213> ORGANISM: Artificial Sequence
<220> FEATURE:
<223> OTHER INFORMATION: MLba, single-stranded oligonucleotide

<400> SEQUENCE: 32
tcgcgagttc gaagagaacc atcagatg                                        28

<210> SEQ ID NO 33
<211> LENGTH: 24
<212> TYPE: DNA
<213> ORGANISM: Artificial Sequence
<220> FEATURE:
<223> OTHER INFORMATION: L228, single-stranded oligonucleotide

<400> SEQUENCE: 33
gcctcgagat aagttgctgg ccag                                            24

<210> SEQ ID NO 34
<211> LENGTH: 24
<212> TYPE: DNA
<213> ORGANISM: Artificial Sequence
<220> FEATURE:
<223> OTHER INFORMATION: C5NH, single-stranded oligonucleotide

<400> SEQUENCE: 34
gctagcggga ctttccattg acgt                                            24

<210> SEQ ID NO 35
<211> LENGTH: 17
<212> TYPE: DNA
<213> ORGANISM: Artificial Sequence
<220> FEATURE:
<223> OTHER INFORMATION: EPC5, single-stranded oligonucleotide

<400> SEQUENCE: 35
ccatggggct gcagaat                                                    17

<210> SEQ ID NO 36
<211> LENGTH: 21
<212> TYPE: DNA

```
<213> ORGANISM: Artificial Sequence
<220> FEATURE:
<223> OTHER INFORMATION: EPC3, single-stranded oligonucleotide

<400> SEQUENCE: 36
ggatcctcat ttttggactg g                                              21

<210> SEQ ID NO 37
<211> LENGTH: 28
<212> TYPE: DNA
<213> ORGANISM: Artificial Sequence
<220> FEATURE:
<223> OTHER INFORMATION: MLhe, single-stranded oligonucleotide

<400> SEQUENCE: 37
tcgcgagcgg ccgcttgcca aacctacg                                       28

<210> SEQ ID NO 38
<211> LENGTH: 27
<212> TYPE: DNA
<213> ORGANISM: Artificial Sequence
<220> FEATURE:
<223> OTHER INFORMATION: MLV-E5, single-stranded oligonucleotide

<400> SEQUENCE: 38
aagcttatgg cgcgttcaac gctctca                                        27

<210> SEQ ID NO 39
<211> LENGTH: 27
<212> TYPE: DNA
<213> ORGANISM: Artificial Sequence
<220> FEATURE:
<223> OTHER INFORMATION: MLV-E3, single-stranded oligonucleotide

<400> SEQUENCE: 39
aagcttctat ggctcgtact ctatagg                                        27
```